United States Patent
Douglas

(10) Patent No.: US 11,003,342 B1
(45) Date of Patent: May 11, 2021

(54) SMART SCROLLING SYSTEM

(71) Applicant: Robert Edwin Douglas, Winter Park, FL (US)

(72) Inventor: Robert Edwin Douglas, Winter Park, FL (US)

( * ) Notice: Subject to any disclaimer, the term of this patent is extended or adjusted under 35 U.S.C. 154(b) by 0 days.

(21) Appl. No.: 16/842,631

(22) Filed: Apr. 7, 2020

Related U.S. Application Data

(63) Continuation-in-part of application No. 16/594,139, filed on Oct. 7, 2019.

(60) Provisional application No. 62/743,837, filed on Oct. 10, 2018.

(51) Int. Cl.
*G06F 3/0484* (2013.01)
*G06F 3/0487* (2013.01)
*G06F 9/54* (2006.01)
*A61B 34/00* (2016.01)

(52) U.S. Cl.
CPC ......... *G06F 3/04845* (2013.01); *A61B 34/74* (2016.02); *G06F 3/0487* (2013.01); *G06F 9/542* (2013.01); *A61B 2034/743* (2016.02); *A61B 2034/744* (2016.02); *G06F 2203/04806* (2013.01)

(58) Field of Classification Search
CPC ................ G01N 2021/8829; G01N 21/95684
See application file for complete search history.

(56) References Cited

U.S. PATENT DOCUMENTS

| | | | |
|---|---|---|---|
| 6,865,718 B2* | 3/2005 | Levi Montalcini ... | G06F 3/0485 715/784 |
| 10,049,625 B1* | 8/2018 | Shanmugasundaram ..................... | G06F 8/38 |
| 2012/0327061 A1* | 12/2012 | Sirpal ................... | G06F 1/1616 345/211 |
| 2014/0107471 A1* | 4/2014 | Haider ................. | A61B 1/3132 600/424 |
| 2014/0282624 A1* | 9/2014 | Holt .......................... | G06T 1/20 719/318 |
| 2019/0146640 A1* | 5/2019 | Barger .................... | G06F 16/22 715/830 |

* cited by examiner

*Primary Examiner* — Ross Varndell

(57) ABSTRACT

This patent discloses a method and apparatus for improving workflow for a radiologist. Specifically, this patent improves the current manual scrolling such as at a constant rate of 0.2 seconds per image slice by establishing triggering events which cause a precise timing system to exactly determine the appropriate amount of time to spend on each image. For example, viewing of homogeneous regions where there is good contrast between a lesion and background will serve as a triggering event for rapid scrolling. In contrast, viewing of heterogeneous and complex regions or regions where the target is similar in gray scale to the background will serve as a triggering event for slow scrolling.

20 Claims, 33 Drawing Sheets

| Slice Number | Complexity (scale of 0-2) | Size of image (0-2) | Presence of pathology on prior examination (+2 seconds) | Finding detected by AI (+2 seconds) | Time spent |
|---|---|---|---|---|---|
| 300 | 0 | 0 | No | No | 0.01 sec |
| 270 | 1 | 1 | No | No | 0.2 sec |
| 150 | 2 | 2 | No | Yes | 2.4 sec |

PRIOR ART

| Slice | Time spent under standard scrolling technique (seconds per slice) |
|---|---|
| 1 | 0.16 |
| 2 | 0.16 |
| 3 | 0.16 |
| 4 | 0.16 |
| 5 | 0.16 |
| 6 | 0.16 |
| 7 | 0.16 |
| 8 | 0.16 |
| 9 | 0.16 |
| 10 | 0.16 |
| 11 | 0.16 |
| 12 | 0.16 |
| 13 | 0.16 |
| 14 | 0.16 |
| 15 | 0.16 |
| 16 | 0.16 |
| 17 | 0.16 |
| 18 | 0.16 |
| 19 | 0.16 |
| 20 | 0.16 |

Figure 2

EXAMPLE LIST OF USER-CONTROLLED REFRESH RATE

EXAMPLE METHODS OF USER INPUTS
- a user-performed finger movement on a rollerball on the mouse
- a user-performed finger movement on a scroll wheel on a mouse
- a user-performed click and drag movement on a mouse
- a user-performed finger strike of an arrow key on a keyboard

EXAMPLES OF WHAT THE METHODS OF USER INPUTS ACCOMPLISHES
- user-desired movement of a single step (e.g. from a first slice to a second slice)
- user-desired movement of multiple steps (e.g., from a first slice to a second slice to a third slice)
- user-desired movement in the forward or reverse direction (e.g., superior to inferior, inferior to superior, etc.)
- user-desired movement of at a fast rate (e.g., two finger scrolling technique on scroll wheel on mouse)
- user-desired movement of at a slow rate (e.g., single finger scrolling technique on scroll wheel on mouse)

EXAMPLE LIST OF USER-CONTROLLED VIEWING PARAMETERS

EXAMPLE METHODS OF USER INPUTS
- a user-performed strike of a hotkey on a keyboard
- a user-performed click and drag movement on a mouse
- a user-performed movement of a scroll wheel on a mouse
- a user-performed point and click on a drop down menu

EXAMPLES OF WHAT THE METHODS OF USER INPUTS ACCOMPLISHES
- a user-desired window and level setting
- a user-desired false color setting
- a user-desired zoom setting
- a user-desired image rotation position
- a user-desired convergence point
- a user-desired viewing angle setting

EXAMPLE LIST OF USER-CONTROLLED REPORTING PARAMETER

EXAMPLE METHODS OF USER INPUTS
- a user-performed strike of a button on a microphone
- a user-performed strike of a hotkey on a keyboard
- a user-performed click and drag movement on a mouse
- a user-performed movement of a scroll wheel on a mouse
- a user-performed point and click on a drop down menu

EXAMPLES OF WHAT THE METHODS OF USER INPUTS ACCOMPLISHES
- a user-desired input of text
- a user-desired alteration of text
- a user-desired deletion of text
- a user-desired navigation from a first section of a report to a second section of a report

LIST OF TRIGGERING EVENTS

- Imaging findings, e.g.,
    - Categorization by AI, e.g.,
        - AI algorithm determines CT head scan is abnormal
        - AI algorithm determines CT head scan is normal
    - Segmented structure (e.g., pituitary stalk) appears on the slice
    - Property of structure being reviewed (e.g., size, heterogeneity vs. homogeneity, etc.)
    - Same imaging feature as prior examination, which showed an abnormality
- Metadata, e.g.,
    - History relevant to particular structure being reviewed (e.g., patient with kidney disease and kidney is being reviewed)
    - Laboratory values are abnormal (e.g., elevated creatinine)
- User eye tracking metric(s), e.g.,
    - Minimum number of fixation points on a particular anatomic structure
- User facial expression recognition metrics, e.g.,
    - Metrics relating to attentiveness
- Report elements
    - Checklist item being viewed
    - Language on report
- Predetermined response criteria (timer-dependent image refresh rate, image-dependent viewing parameter, image-dependent reporting parameter)
- Any combination of the above

THREE CATEGORIES OF PREDETERMINED RESPONSES

Category #1 timer-dependent image refresh rate

Category #2 image-dependent viewing parameter

Category #3 image-dependent reporting parameter

PREDETERMINED RESPONSES CATEGORY #1
TIMER-DEPENDENT IMAGE REFRESH RATE (SLIDE 1 OF 3)

The first timer-dependent image refresh rate causes a pause at a single image for a minimum period of time

- Assume the user controlled scrolling rate is to see each image for 0.16 seconds per slice. The timer-dependent refresh rate when triggered causes a pause of 1.00 seconds. After this minimum period of time has passed, the refresh rate the user-controlled refresh rate (0.16 seconds per slice) resumes. This is useful by forcing the user to slow down on when triggering event (e.g., triggering event is the detection by an AI algorithm of a small pulmonary nodule on only a single slice), which could otherwise easily be missed by a user. Thus, a triggering event has caused the predetermined response of the timer-dependent image refresh rate to pause at a single image for a minimum period of time.

The second timer-dependent image refresh rate utilized for at least two consecutive images wherein the timer-dependent image refresh rate is slower than the user-controlled refresh rate

- Assume the user controlled scrolling rate is to see each image for 0.16 seconds per slice. The timer-dependent refresh rate when triggered causes a pause of 1.00 seconds on two consecutive slices. After the 1.00 second pause on the first slice, the second slice is displayed. After the 1.00 second pause on the second slice, the user-controlled refresh rate (0.16 seconds per slice) resumes for the third slice and onward. This is useful by forcing the user to slow down on an important finding (e.g., triggering event is the detection by an AI algorithm of a small pulmonary nodule on two slices), which could otherwise easily be missed by a user. Thus, a triggering event has caused the predetermined response of the timer-dependent image refresh rate to be utilized for at least two consecutive images wherein the timer-dependent image refresh rate is slower than the user-controlled refresh rate.

The third timer-dependent image refresh rate utilized for at least two consecutive images wherein the timer-dependent image refresh rate is faster than the user-controlled refresh rate

- Assume the user controlled scrolling rate is to see each image for 0.16 seconds per slice. The timer-dependent refresh rate when triggered causes a pause of 0.01 seconds on two consecutive slices. After the 0.01 second pause on the first slice, the second slice is displayed. After the 0.01 second pause on the second slice, the user-controlled refresh rate (0.16 seconds per slice) resumes. This is useful by forcing the user to speed up on an non-important data (e.g., triggering event is the detection by an AI algorithm of an air gap above the patients head on a head CT scan). This contains no data and the radiologist need not spend valuable seconds while scrolling through the air gap above the head until he/she reaches the scalp. Thus, a triggering event has caused the predetermined response of the timer-dependent image refresh rate to be utilized for at least two consecutive images wherein the timer-dependent image refresh rate is faster than the user-controlled refresh rate.

PREDETERMINED RESPONSES CATEGORY #1
TIMER-DEPENDENT IMAGE REFRESH RATE (SLIDE 2 OF 3)

The fourth timer-dependent image refresh rate utilized only a limited number of times, such that after the limited number of times is exceeded, the refresh rate is user-controlled
- First, assume the user controlled scrolling rate is to see each image for 0.16 seconds per slice. The timer-dependent refresh rate when a triggering event causes a pause of 1.00 seconds. After this minimum period of time has passed, the refresh rate the user-controlled refresh rate (0.16 seconds per slice) resumes.
- Next, assume that the user scrolls back over the same slice that triggering event causes a pause of 1.00 seconds. An option at this juncture is to no longer require the 1.00 second delay, so that the second time the slice is presented, it is shown for 0.16 seconds (not 1.00 seconds).
- This is useful by forcing the user to slow down on an important finding (e.g., triggering event is the detection by an AI algorithm of a small pulmonary nodule on only a single slice), which could otherwise easily be missed by a user. Once the user characterizes it, it would be useful to have the option to no longer require the 1.00 second delay so as to speed interpretation.
- Thus, a triggering event has caused the predetermined response of the timer-dependent image refresh rate to be utilized only a limited number of times as described.

The fifth timer-dependent image refresh rate is variable wherein a first image refresh rate is utilized when a first set of images are first presented and wherein a second image refresh rate is utilized when the first set of images are second presented
- First, assume the user controlled scrolling rate is to see each image for 0.16 seconds per slice. The timer-dependent refresh rate when triggered causes a pause of 1.00 seconds. After this minimum period of time has passed, the refresh rate the user-controlled refresh rate (0.16 seconds per slice) resumes.
- Next, assume that the user scrolls back over the same slice that triggered a pause of 1.00 seconds. An option at this juncture is to reduce the length of the delay to somewhere in between 0.16 seconds and 1.00 seconds.
- This is useful by forcing the user to slow down on an important finding (e.g., triggering event is the detection by an AI algorithm of a small pulmonary nodule on only a single slice), which could otherwise easily be missed by a user. Once the user characterizes it, it would be useful to have a shorter period of time where the image was displayed (e.g., between 0.16 seconds and 1.00 seconds) so as to speed interpretation.
- Thus, a triggering event has caused the predetermined response of the timer-dependent image refresh rate to be variable as described.

PREDETERMINED RESPONSES CATEGORY #1
TIMER-DEPENDENT IMAGE REFRESH RATE (SLIDE 3 OF 3)

The sixth timer-dependent refresh rate is user-dependent wherein a first set of images is presented to a first user at a first timer-dependent image refresh rate and the first set of images is presented to a second user at a second timer-dependent image refresh rate
- First, assume that there are two different users. User #1 has a first preference. User #2 has a second preference. The first preference and second preference are different. User #1 sets a first preference for a 1.00 second delay each time a certain triggering event occurs (e.g., triggering event is the detection by an AI algorithm of a small pulmonary nodule on only a single slice), which could otherwise easily be missed by a user. User #2 sets a different preference setting as compared to user #1. For example, User #2 sets a 1.50 second delay each time the same triggering event occurs (e.g., triggering event is the detection by an AI algorithm of a small pulmonary nodule on only a single slice), which could otherwise easily be missed by a user.
- Thus, a triggering event (e.g., triggering event is the detection by an AI algorithm of a small pulmonary nodule on only a single slice) has caused the predetermined response of the timer-dependent image refresh rate to be different in user #1 as compared to user #2.
- This is useful because different users may have different abilities or personal preferences. Additionally, the same user could choose to the timer-dependent refresh rates for a variety of other reasons, such as the time of the day.
- Thus, a triggering event has caused the predetermined response of the timer-dependent image refresh rate to be user-dependent as described.

The seventh timer-dependent refresh rate is independent of the user-inputted image refresh rate
- First, assume that a user wants to do a hands off approach and is therefore not scrolling and also assume that some of the slices are tied to triggering events and some of the slices are not tied to triggering events. This is discussed in detail in Figure 22.
- This is useful because different users may have different preferences. Additionally, the same user could choose to the timer-dependent refresh rates for a variety of other reasons or allow the timer-dependent refresh rate to be determined by an AI algorithm.
- Thus, a triggering event has caused the predetermined response of the timer-dependent image refresh rate to be independent of user-inputted image refresh rate.

PREDETERMINED RESPONSES CATEGORY #2
IMAGE-DEPENDENT VIEWING PARAMETER (SLIDE 1 OF 4)

The first image-dependent viewing parameter performs conventional windowing and leveling for the entire dataset

- First, assume the radiologist has applied a first window and level setting to the entire CT abdomen and pelvis dataset. Assume that the radiologist has completed all checklist items that required the first window and level setting and is now moving to a subsequent item on the checklist that requires a second window and level setting. The triggering event (e.g., moving to a item on the checklist linked (e.g., see processing block 302 in Figure 3) to a preferred window and level setting different from the current window and level setting) has caused the predetermined response of the image dependent viewing parameter of performing conventional windowing and leveling for the entire dataset. For example, after the last checklist item is reviewed using the standard window and level setting for the abdomen, the radiologist may elect to move to the bone items on the checklist. The action of moving to the next item on the checklist itself can act as a triggering event.

- This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling.

- Thus, a triggering event has caused the predetermined response of the image-dependent viewing parameter to perform conventional windowing and leveling for the entire dataset.

The second image-dependent viewing parameter sets a window and level parameter for a first image slice independently from a window and level parameter for a second image slice

- First, assume that the radiologist is scrolling through the liver with a standard liver window and level setting. Assume that there an triggering event (e.g., a mass lesion in the liver discovered by an AI algorithm with similar Hounsfield Units to normal liver parenchyma).
- This is useful because it instantly provides an improved visual analysis of the mass lesion identified by the AI algorithm and saves the step of detection, saves the step of mentally deciding whether to window and level, saves the step of user-performed striking a hotkey, saves the step of mouse click and drag for windowing and leveling.
- Thus, a triggering event has caused the predetermined response of the image-dependent viewing parameter to set a window and level parameter for a first image slice independently from a window and level parameter for a second image slice.

PREDETERMINED RESPONSES CATEGORY #2
IMAGE-DEPENDENT VIEWING PARAMETER (SLIDE 2 OF 4)

The third image-dependent viewing parameter includes displaying simultaneously a first visual representation adjustment logic for a first segmented structure and a second visual representation adjustment logic for a second segmented structure wherein the first visual representation adjustment logic is different from the second visual representation adjustment logic

- First, assume the radiologist now moving to the pancreas, which is notoriously a difficult region to identify pathology because the pathologic lesion is commonly only a few Hounsfield Units different from normal pancreas tissue. The triggering event (e.g., moving to a item on the pancreas checklist item) has caused the predetermined response of the image dependent viewing parameter of performing dual windowing and leveling, as disclosed in US Patent 10, 584,400. For example, after the spleen checklist item is reviewed using the standard window and level setting for the abdomen, the radiologist may elect to move to the pancreas on the checklist. The action of moving to the next item on the checklist itself can act as a triggering event.

- This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling.

- Thus, a triggering event has caused the predetermined response of the image-dependent viewing parameter to perform dual windowing and leveling for the pancreas.

The fourth image-dependent viewing parameter is a false color setting

- First, assume the radiologist is viewing volume rendered images on a 2D monitor. Assume that the radiologist prefers a color schematic wherein the blood vessels are light pink colored when they are not actively being examined (e.g., such as when the radiologist is reviewing the bones), but appear bright red when actively being examined. The triggering event is the action of moving from the bones item on the checklist to the blood vessel item on the checklist. The predetermined response of the image dependent viewing parameter is the implementation of red false color of the blood vessels.

- This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling.

- Thus, a triggering event has caused the predetermined response of the image-dependent viewing parameter to perform false color.

PREDETERMINED RESPONSES CATEGORY #2
IMAGE-DEPENDENT VIEWING PARAMETER (SLIDE 3 OF 4)

The fifth image-dependent viewing parameter of performing zooming
- First, assume the radiologist is viewing a stack of CT slices through the lungs and a triggering event (e.g., a small 5 mm pulmonary nodule detected by an AI algorithm on the image slice) occurs. This small pulmonary nodule is seen by the radiologist in an un-zoomed image, but the radiologist needs to zoom in to better characterize it. In this example, the triggering event of the small pulmonary nodule appearing on the screen causes the predetermined response of an image-dependent viewing parameter of performing the action of zooming.
- This is useful because it instantly provides an improved visual analysis of the small finding and saves the step of detection, saves the step of mentally deciding whether to zoom, saves the step of user-performed striking a hotkey, saves the step of mouse click and drag.
- Thus, a triggering event has caused the predetermined response of the image-dependent viewing parameter to perform zooming.

The sixth image-dependent viewing parameter is an image rotation
- First, assume a triggering event (e.g., a small fracture of the posterior malleolus of the tibia enters the field of view on an axial slice). This small fracture is seen by the radiologist, but the radiologist needs to better characterize it with a volume rendered image. In this example, the triggering event causes the predetermined response of an image-dependent viewing parameter of performing the action of generating a side panel on the radiology monitor with a volume rendered image of the posterior malleolus with a rotation.
- This is useful because it instantly provides an improved visual analysis of the small finding and saves the step of detection, saves the step of mentally deciding whether to create volume rendered images, saves the step of user-performed striking a hotkey, saves the step of mouse click and drag to rotate.
- Thus, a triggering event has caused the predetermined response of the image-dependent viewing parameter to perform image rotation.

PREDETERMINED RESPONSES CATEGORY #2
IMAGE-DEPENDENT VIEWING PARAMETER (SLIDE 4 OF 4)

The seventh image-dependent viewing parameter is a viewing angle setting
- First, assume a triggering event (e.g., a small fracture of the posterior malleolus of the tibia enters the field of view on an axial slice). This small fracture is seen by the radiologist, but the radiologist needs to better characterize it with a volume rendered image. In this example, the triggering event causes the predetermined response of an image-dependent viewing parameter of performing the action of generating a side panel on the radiology monitor with a volume rendered image of the posterior malleolus with six viewing positions (from top, from bottom, from left, from right, from front, from back), all of which have viewing angles directed toward the fracture.
- This is useful because it instantly provides an improved visual analysis of the small finding and saves the step of detection, saves the step of mentally deciding whether to create volume rendered images, saves the step of user-performed striking a hotkey, saves the step of mouse click and drag to rotate.
- Thus, a triggering event has caused the predetermined response of the image-dependent viewing parameter to generate viewing angles.

The eighth image-dependent viewing parameter includes advanced image processing techniques
- First, assume a radiologist is viewing contiguous cross-sectional imaging slices and a triggering event (e.g., detection by an AI algorithm of a small pulmonary nodule on only a single slice) occurs. This small nodule is seen by the radiologist, but the radiologist needs to better characterize it with advanced image processing techniques. In this example, the triggering event causes the predetermined response of at least one of the group of: viewing on an extended reality display; 3D cursor usage (see US Patent Application 15/878,463; virtual tool usage (see PCT/US19/47891); voxel manipulation (see US Patent application #16/195,251); and, incorporating data unit assurance markers (see US Patent Application 16/785,506).
- This is useful because it instantly provides an improved visual analysis of the small finding and saves the step of detection, saves the step of mentally deciding whether to create volume rendered images, saves the step of user-performed striking a hotkey, saves the step of mouse click and drag to rotate.
- Thus, a triggering event has caused the predetermined response of the image-dependent viewing parameter to generate advanced image processing techniques.

PREDETERMINED RESPONSES CATEGORY #3
IMAGE-DEPENDENT REPORTING PARAMETER (SLIDE 1 OF 2)

The first image-dependent reporting parameter wherein text is automatically inputted into a section of a report
- First, assume a radiologist is viewing contiguous axial cross-sectional imaging slices and a triggering event (e.g., detection by an AI algorithm of a pulmonary nodule in the right lung that measures 5 mm in greatest axial dimension) occurs. In this example, the triggering event causes the predetermined response of an image-dependent reporting parameter of performing the action of entering text stating "5 mm right lung pulmonary nodule".
- This is useful because it saves time of entering report text and also prevents any accidental omission (e.g., the radiologist intended to describe the pulmonary nodule, but perhaps got distracted from a phone call and therefore never inserted the text describing the pulmonary nodule into the report).
- Thus, a triggering event has caused the predetermined response of the image-dependent reporting parameter to insert text into the radiology report.

The second image-dependent reporting parameter wherein text in a section of a report is automatically altered
- Next, consider continuing with the example above wherein the text stating "5 mm right lung pulmonary nodule". Consider now, that viewing is of contiguous coronal imaging slices and a triggering event (e.g., detection by an AI algorithm of the same pulmonary nodule in the right lung as above, but it measures 7 mm in greatest coronal dimension) occurs. In this example, the triggering event causes the predetermined response of an image-dependent reporting parameter of performing the action of automatically altering text to state "7 mm right lung pulmonary nodule", not "5 mm right lung pulmonary nodule".
- This is useful because it saves time of altering report text and also prevents any accidental omission (e.g., the radiologist intended to alter the size of the pulmonary nodule, but perhaps got distracted from a phone call and therefore never inserted the text describing the pulmonary nodule into the report).
- Thus, a triggering event has caused the predetermined response of the image-dependent reporting parameter to alter text into the radiology report.

PREDETERMINED RESPONSES CATEGORY #3
IMAGE-DEPENDENT REPORTING PARAMETER (SLIDE 2 OF 2)

The third image-dependent reporting parameter wherein text in a section of a report is automatically deleted
- First, assume a radiologist is viewing contiguous axial cross-sectional imaging slices of the femur and a triggering event (e.g., detection by an AI algorithm of a bone lucency determined to be 50% likely to represent a fracture and 50% likely to represent a nutrient foramen) occurs. In this example, the triggering event causes the predetermined response of an image-dependent reporting parameter of performing the action of entering text stating "lucency in femur, which may represent a fracture or nutrient foramen". Next, assume that the contiguous sagittal images are reviewed and a second triggering event occurs (e.g., detection by an AI algorithm of a bone lucency determined to be 100% likely to represent a fracture). In this example, the second triggering event causes the predetermined response of an image-dependent reporting parameter of performing the action of deleting text (i.e., ~~lucency in~~ femur~~, which may represent a~~ fracture ~~or nutrient foramen~~) such that the report now states "femur fracture".
- This is useful because it saves time of deleting report text and also prevents any accidental inclusion of text that was not meant to make it to the report (e.g., the radiologist intended to describe the pulmonary nodule, but perhaps got distracted from a phone call and therefore never inserted the text describing the pulmonary nodule into the report).
- Thus, a triggering event has caused the predetermined response of the image-dependent reporting parameter to deleting text into the radiology report.

The fourth image-dependent reporting parameter wherein a cursor is automatically moved from a first section of a report to a second section of a report.
- First, assume a radiologist is viewing contiguous axial cross-sectional imaging slices of the abdomen and a triggering event (e.g., axial cross-sectional imaging slices include the kidney) occurs. In this example, the triggering event causes the predetermined response of an image-dependent reporting parameter of performing the action of moving the cursor from a first section of the report (e.g., adrenal gland section) to a second section of a report (e.g., kidney section).
- This is useful because it saves time of manually switching between sections.
- Thus, a triggering event has caused the predetermined response of the image-dependent reporting parameter to switch to a new section of the radiology report.

| Triggering Event | Example predetermined response for timer-dependent image refresh rate | |
|---|---|---|
| | Use slow timer-dependent image refresh rate if triggering event shows ... | Use slow timer-dependent image refresh rate if triggering event shows ... |
| Size of image | Large image size | Small image size |
| Complexity of image | High complexity (e.g., heterogeneous image) | Homogeneous image |
| Contrast between background and pathology | Low contrast (e.g., pathologic lesion and organ from which it arises are similar in Hounsfield Units) | Low contrast (e.g., pathologic lesion and organ from which it arises are similar in Hounsfield Units) |
| Probability of pathology in the image | High | Low probability |
| Severity of pathology expected in the image | More severe pathology is expected in the image | More benign pathology is expected in the image |
| Radiologist's personal characteristics (preference, eye sight, age) | Variable | Variable |
| External characteristics (time of day) | Variable | Variable |

Figure 19

| Slice | Triggering event | Notification of Triggering Event | Timer-dependent image refresh rate (i.e., how much time is spent on each slice) |
|---|---|---|---|
| 1 | No | N/A | 0.16 seconds |
| 2 | No | N/A | 0.16 seconds |
| 3 | No | N/A | 0.16 seconds |
| 4 | Prior exam showed an abnormality at this location | No | 2.00 seconds |
| 5 | No | N/A | 0.16 seconds |
| 6 | No | N/A | 0.16 seconds |
| 7 | AI detected an abnormality at this slice | Red circle markup | 3.50 seconds |
| 8 | No | N/A | 0.16 seconds |
| 9 | No | N/A | 0.16 seconds |
| 10 | No | N/A | 0.16 seconds |
| 11 | Slice contains anatomy relevant to clinical history | No | 1.00 seconds |
| 12 | No | N/A | 0.16 seconds |
| 13 | No | N/A | 0.16 seconds |
| 14 | Slice contains anatomic structure needing careful review | No | 1.50 seconds |
| 15 | No | N/A | 0.16 seconds |
| 16 | No | N/A | 0.16 seconds |
| 17 | No | N/A | 0.16 seconds |
| 18 | No | N/A | 0.16 seconds |
| 19 | Slice does not contain patient data | No | 0.00 seconds |
| 20 | Slice does not contain patient data | No | 0.00 seconds |

Figure 22

Fig. 23A
| Slice Number | Complexity (scale of 0-2) | Size of image (0-2) | Presence of pathology on prior examination (+2 seconds) | Finding detected by AI (+2 seconds) | Time spent |
|---|---|---|---|---|---|
| 300 | 0 | 0 | No | No | 0.01 sec |
| 270 | 1 | 1 | No | No | 0.2 sec |
| 150 | 2 | 2 | No | Yes | 2.4 sec |
Fig. 23B
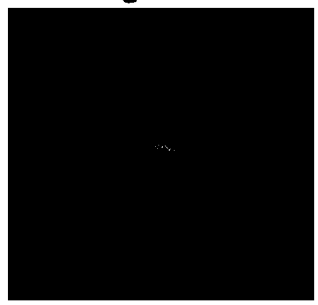
Fig. 23C
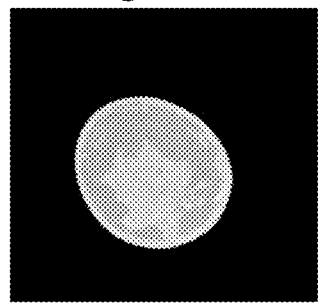
Fig. 23D
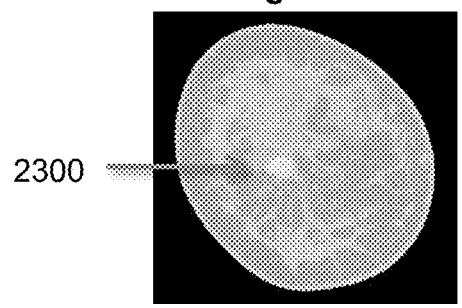

Fig. 25A
Fig. 25B
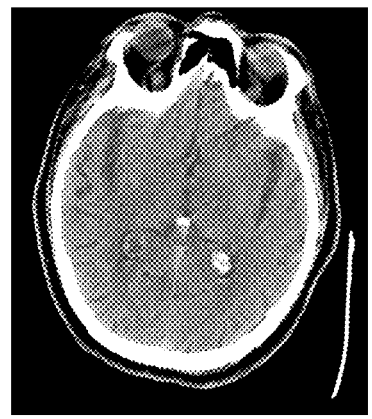
Fig. 25C
Fig. 25D
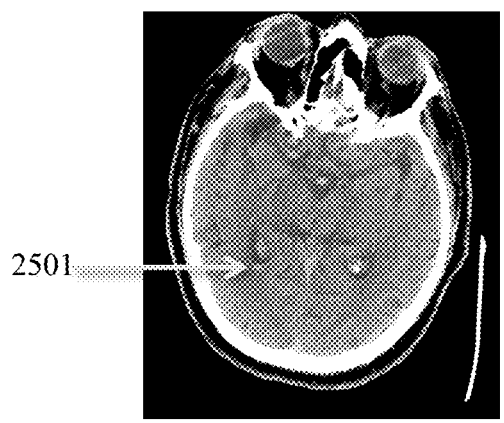
2501
2502
Fig. 25E
Fig. 25F
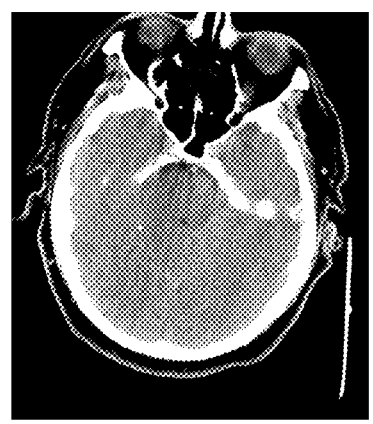

Fig. 29A
Examples of image-dependent viewing parameters for advanced viewing on Extended Reality Displays
- Rotating volume
- Changing location of viewing perspective
- Zooming
- Converging
2900
Fig. 29B
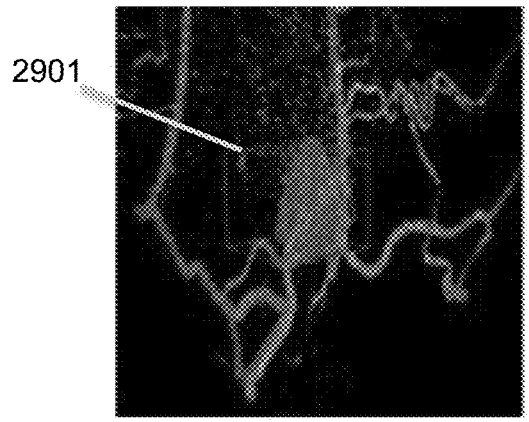
Fig. 29C
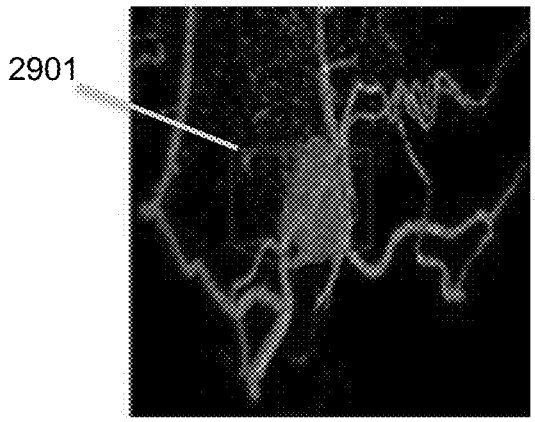
Fig. 29D
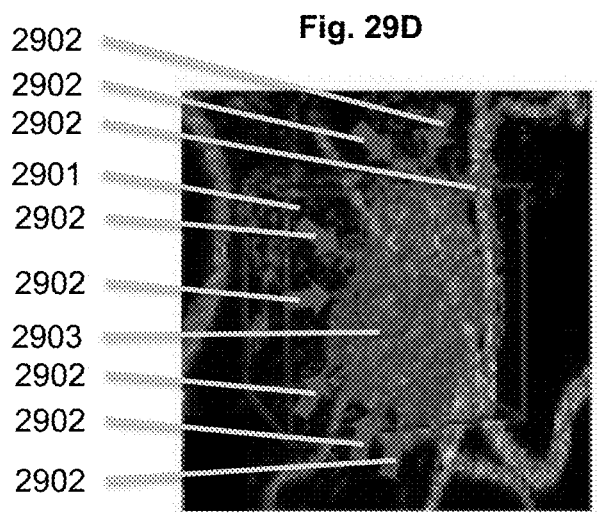
Fig. 29E
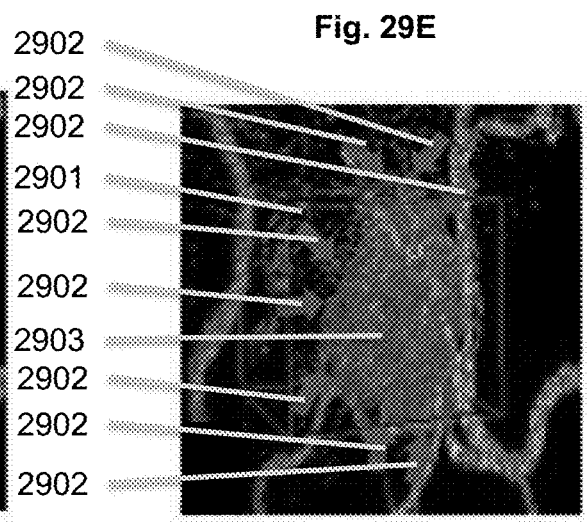

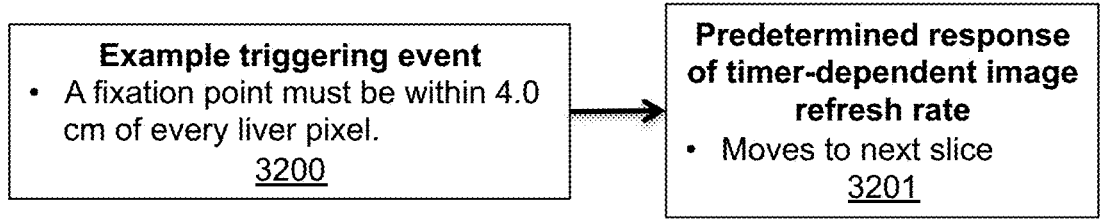
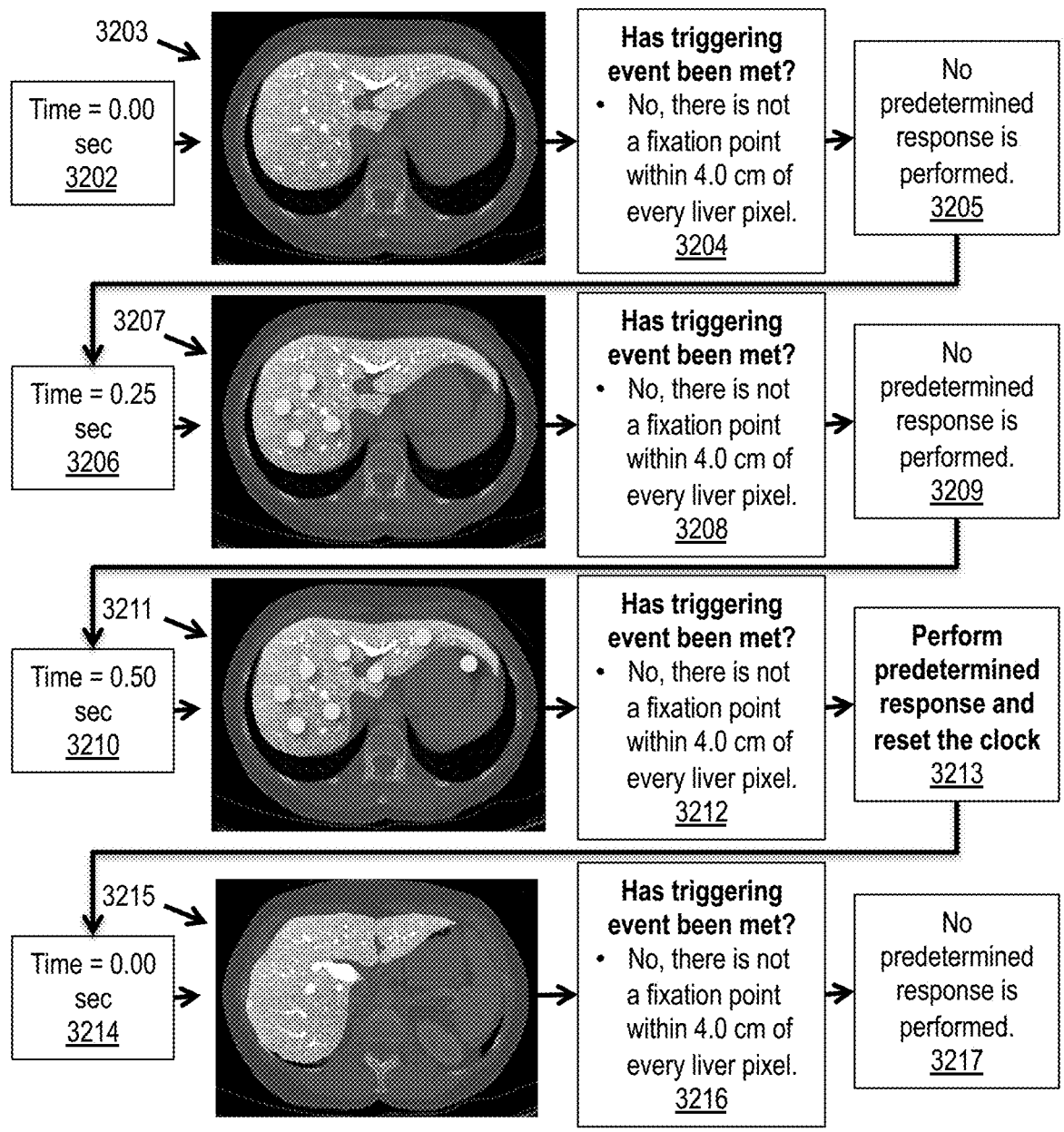

| Time | Displayed image (viewing settings) | Fixation points | Report |
|---|---|---|---|
| 0.00 - 3.00 seconds | Whole image has WL 3000, WW 30000 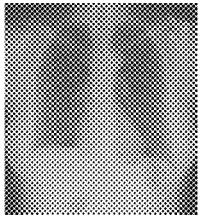 | 5 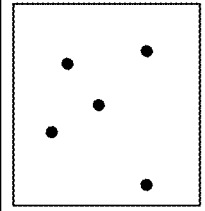 | Trachea: [ ]<br>Lungs: [ ]<br>Heart: [ ] |
| 3.00 - 9.00 seconds | Zoomed in and dual windowing on trachea 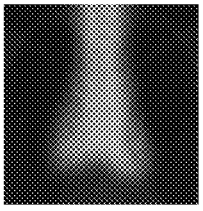 | 10 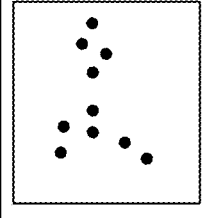 | Trachea: [Normal]<br>Lungs: [ ]<br>Heart: [ ] |
| 9.00 - 20.00 seconds | Zoom in on each lung and dual windowing on lung 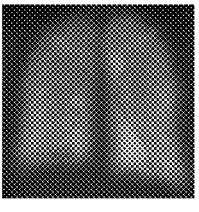 | 20 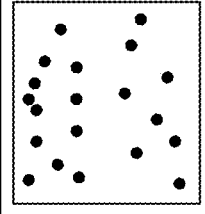 | Trachea: [Normal]<br>Lungs: [Right lung pulmonary nodule]<br>Heart: [ ] |
| 20.00 - 25.00 seconds | Zoom in on each heart and dual windowing on heart 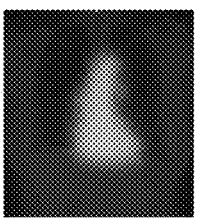 | 15 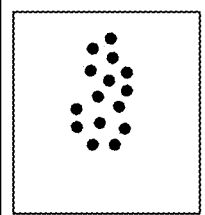 | Trachea: [Normal]<br>Lungs: [Right lung pulmonary nodule]<br>Heart: [Normal] |

Figure 33

SMART SCROLLING SYSTEM

TECHNICAL FIELD

Aspects of this disclosure are generally related to improving scrolling techniques on a mouse.

BACKGROUND

There is considerable pressure on radiologists to review a large quantity of medical images within tight time constraints. A typical case might have 500 axial, 500 sagittal and 500 coronal slices for a total of 1,500 slices to be viewed for each case. A radiologist must rapidly scroll through these images using a computer mouse with a wheel button. The radiologist may use a one finger or two finger technique. To meet the time constraints the radiologist might only be able to spend 0.25 seconds per slice.

SUMMARY

All examples, aspects and features mentioned in this document can be combined in any technically possible way.

The purpose of this patent is to provide an improved method of viewing and reporting on medical images. A method, software suite and apparatus are disclosed.

With respect to reviewing images, the method presents images to a user at a user-controlled image refresh rate, generates a triggering event wherein the triggering event is associated with a timer-dependent image refresh rate, monitors for the triggering event and when the triggering event occurs, presenting images to the user at the timer-dependent image refresh rate.

Some embodiments comprise wherein the user controlled image refresh rate is performed by at least one of the group comprising: a rollerball on the mouse; a scroll wheel on a mouse; a click and drag movement on a mouse; and, arrow keys on a keyboard.

Some embodiments comprise wherein the triggering event comprises at least one of the group of: an imaging finding; an aspect of patient metadata; user eye tracking metrics; predetermined responses; report elements; and, user facial recognition metrics.

Some embodiments comprise wherein the timer-dependent image refresh rate comprises at least one of the group of comprising: a first timer-dependent image refresh rate causes pausing at a single image for a minimum period of time wherein after the minimum period of time has passed, the refresh rate the user-controlled refresh rate resumes; a second timer-dependent image refresh rate utilized for at least two consecutive images wherein the second timer-dependent image refresh rate is slower than the user-controlled refresh rate; a third timer-dependent image refresh rate utilized for at least two consecutive images wherein the third timer-dependent image refresh rate is faster than the user-controlled refresh rate; a fourth timer-dependent image refresh rate utilized only a limited number of times, such that after the limited number of times is exceeded, the refresh rate is user-controlled; a fifth timer-dependent image refresh rate wherein the fifth timer-dependent image refresh rate is variable wherein a first image refresh rate is utilized when a first set of images are first presented and wherein a second image refresh rate is utilized when the first set of images are second presented; a sixth timer-dependent image refresh rate wherein the sixth timer-dependent image refresh rate is user-dependent wherein a first set of images is presented to a first user at a first timer-dependent image refresh rate and the first set of images is presented to a second user at a second timer-dependent image refresh rate; and a seventh timer-dependent refresh rate wherein the seventh timer-dependent image refresh rate is independent of the user-controlled image refresh rate.

Some embodiments comprise wherein a user notification is presented when a triggering event occurs wherein the user notification comprises at least one of the group of: visual annotation marker on the image; visual image manipulation techniques; auditory notification; and, tactile notification.

Some embodiments comprise wherein the images comprise at least one of the group comprising: cross-sectional images; volume rendered images; and, images displayed on an extended reality headset.

Some embodiments comprise an opportunity to turn off monitoring of the triggering event.

Some embodiments comprise presenting images to a user at a user-controlled viewing parameter, generating a triggering event wherein the triggering event is associated with an image-dependent viewing parameter, monitoring for the triggering event and when the triggering event occurs, presenting the images to the user with the image-dependent viewing parameter.

Some embodiments comprise wherein the user-controlled viewing parameter is performed by at least one of the group comprising: a user-performed strike of a hotkey on a keyboard; a user-performed click and drag movement on a mouse; a user-performed movement of a scroll wheel on a mouse; and a user-performed point and click on a drop down menu. The purpose of the performance of the maneuvers is to achieve at least one of the group comprising: a user-desired window and level setting; a user-desired false color setting; a user-desired zoom setting; a user-desired image rotation position; a user-desired convergence point; a user-desired viewing angle setting; and a user-desired manipulation of voxels.

Some embodiments comprise wherein the triggering event comprises at least one of the group of: an imaging finding; an aspect of patient metadata; user eye tracking metrics; predetermined responses; report elements; and, user facial recognition metrics.

Some embodiments comprise wherein the image-dependent viewing parameter comprises at least one of the group of comprising: a first image-dependent viewing parameter wherein the first image-dependent viewing parameter is a window width and window level setting for the entire dataset; a second image-dependent viewing parameter wherein the second image-dependent viewing parameter includes setting a window and level parameter for a first image slice independently from a window and level parameter for a second image slice; a third image-dependent viewing parameter wherein the third image-dependent viewing parameter includes displaying simultaneously a first visual representation adjustment logic for a first segmented structure and a second visual representation adjustment logic for a second segmented structure wherein the first visual representation adjustment logic is different from the second visual representation adjustment logic; a fourth image-dependent viewing parameter wherein the fourth image-dependent viewing parameter is a false color setting; a fifth image-dependent viewing parameter wherein the fifth image-dependent viewing parameter is a zoom setting; a sixth image-dependent viewing parameter wherein the sixth image-dependent viewing parameter is an image rotation setting; a seventh image-dependent viewing parameter wherein the seventh image-dependent viewing parameter is a viewing angle setting; and an eighth image-dependent viewing parameter wherein the eight image-dependent viewing parameter includes advanced image processing techniques.

Some embodiments comprise wherein a user notification is presented when a triggering event occurs wherein the user notification comprises at least one of the group of: visual annotation marker on the image; visual image manipulation techniques; auditory notification; and, tactile notification.

Some embodiments comprise wherein the images comprise at least one of the group comprising: cross-sectional images; volume rendered images; and, images displayed on an extended reality headset.

Some embodiments comprise an opportunity to turn off monitoring of the triggering event.

Some embodiments comprise presenting an image reporting system to a user with user-controlled reporting parameters, generating a triggering event wherein the triggering event is associated with an image-dependent reporting parameter, monitoring for the triggering event and when the triggering event occurs, presenting the image reporting system to the user with the image-dependent reporting parameter.

Some embodiments comprise wherein the user-controlled reporting parameter is performed by at least one of the group comprising: a user-performed strike of a button on a microphone; a user-performed strike of a hotkey on a keyboard; a user-performed click and drag movement on a mouse; a user-performed movement of a scroll wheel on a mouse; and a user-performed point and click on a drop down menu. The purpose of the user inputs is to achieve at least one of the group comprising: a user-desired input of text; a user-desired alteration of text; a user-desired deletion of text; and a user-desired navigation from a first section of a report to a second section of a report.

Some embodiments comprise wherein the triggering event comprises at least one of the group of: an imaging finding; an aspect of patient metadata; user eye tracking metrics; and, user facial recognition metrics.

Some embodiments comprise wherein the image-dependent reporting parameter comprises at least one of the group of comprising: a first image-dependent reporting parameter wherein text is automatically inputted into a section of a report; a second image-dependent reporting parameter wherein text in a section of a report is automatically altered; a third image-dependent reporting parameter wherein text in a section of a report is automatically deleted; and a fourth image-dependent reporting parameter wherein a cursor is automatically moved from a first section of a report to a second section of a report.

Some embodiments comprise wherein a user notification is presented when a triggering event occurs wherein the user notification comprises at least one of the group of: visual annotation marker on the image; visual image manipulation techniques; auditory notification; and, tactile notification.

Some embodiments comprise wherein the images comprise at least one of the group comprising: cross-sectional images; volume rendered images; and, images displayed on an extended reality headset.

Some embodiments comprise an opportunity to turn off monitoring of the triggering event.

Some embodiments comprise a method of reviewing images and reporting comprising: presenting images to a user at a user-controlled image refresh rate and user-controlled viewing parameter; presenting an image reporting system to the user with user-controlled reporting parameters; generating a first triggering event wherein the first triggering event is associated with a timer-dependent image refresh rate; generating a second triggering event wherein the second triggering event is associated with an image-dependent viewing parameter; generating a third triggering event wherein the third triggering event is associated with an image-dependent reporting parameter; monitoring for the first triggering event; monitoring for the second triggering event; monitoring for the third triggering event; when the first triggering event occurs, presenting the images to the user at the timer-dependent image refresh rate; when the second triggering event occurs, presenting the images to the user with the image-dependent viewing parameter; and when the third triggering event occurs, presenting the image reporting system to the user with the image-dependent reporting parameter.

Types of patient medical condition data would include but, not be limited to: doctor's examination data; patient's health records; artificial intelligence (AI)/machine learning; patient's responses to medical personnel questioning; and medical images taken in previous visits to the hospital or medical imaging facility.

To illustrate this linking several examples are provided. If the patient presents with shortness of breath, the medical image slices containing portions of the lungs could be treated as explained in the embodiments that follow. If the patient presented with pain in the chest, the medical image slices containing portions of the heart could be treated as explained in the embodiments that follow. If the patient presented with pain in the abdomen, the medical image slices containing portions of the abdomen and appendix could be treated as explained in the embodiments that follow. If the patient in for a scheduled appointment for follow up on status of a tumor, the medical images from a previous imaging session could be retrieved and displayed in conjunction with currently obtained medical images.

In some embodiments, the scrolling process would automatically pause for a period of time the duration of which could be specified by the individual radiologist, best practices of the medical facility or derived from studies regarding miss rate as a function of viewing time. The pause would, in the preferred embodiment, override the finger scrolling technique. Therefore, even if the finger were still moving on the scroll wheel, the same image (e.g., a single axial slice) would remain on the screen for a period of pause time. This would allow the radiologist additional saccades eye movements and additional fixation points on the screen for that particular slice. The pause can be event triggered. Triggering events include, but are not limited to the following: AI detected abnormality; specific anatomic feature which is known to require additional time for review; and, same slice as prior exam wherein a lesion was identified and marked. Other triggering events are discussed in the figures.

In some embodiments, a portion of the image slice(s) could be highlighted through change of contrast (e.g., increasing contrast in some region pertaining to pertinent patient medical condition data or subduing contrast in regions not related to pertinent patient medical condition data).

In some embodiments, external symbols could be employed to annotate the slice(s) of the region(s) pertaining to the patient medical condition data. Examples of the external symbols would include but, not be limited to the following: an arrow, circle, or image slice boundary change colors.

In some embodiments, medical image slice(s) could blink as a signal to the radiologist that of the region(s) pertaining to the patient medical condition data was about to be viewed so that the radiologist could self modify the scrolling and/or viewing technique. As an example, rather than relying on the saccadian pattern to detect anomalies such as small tumors, he/she could use the finger tracing technique.

In some embodiments, an external device could be attached to the radiologist viewing system which give an audio signal when the radiologist was scrolling through a slicer(s) of the region(s) pertaining to the patient medical condition data. In some embodiments, an external device could be attached to the radiologist viewing system which give a tactile signal when the radiologist was scrolling through a slicer(s) of the region(s) pertaining to the patient medical condition data. The audio and tactile devices could be combined in a system such as a buzzer.

In some embodiments, the medical image data could be segmented into the regions/organs within the body. This would include but, not be limited to: heart, lungs, liver, kidney, bone structure, stomach, intestines, spleen—all of the specific items on the medical facility check list. These segmented regions presented to the radiologist by various means such as but not limited to: called by a pull down menu; audio command by radiologist; arranged in sequence of the check list; arranged in priority of the region(s) pertaining to the patient medical condition data.

In some embodiments, the radiologist may set a scroll rate which would obviate the need for the two-finger scroll. This rate would be under the control of the viewing radiologist and he/she could have multiple scroll rate default values depending on type of medical images, check list item, type of view (e.g., sagittal vs. coronal). The scroll rate could automatically change in region(s) pertaining to the patient medical condition data. The scrolling could be interrupted by the radiologist at any time by interactions with the workstation through the keyboard, mouse or verbal command.

In some embodiments, the medical image slice data could be combined to form volumetric data per U.S. Pat. No. 8,384,771 and displayed in 3D for the radiologist. This volumetric data would nominally be segmented and filtered in accordance with the medical facility checklist. Under these conditions the scrolling could change the viewing position of the radiologist with respect to the volumetric data. At the radiologist option, the scrolling could be done automatically for all four sides, top, bottom. The scroll rate could also automatically change in region(s) pertaining to the patient medical condition data. In some embodiments, the segmentation process described above could be combined with enlarging the regions/organs presented on the radiologist display) pertaining to the patient medical condition data.

Each of these specific actions with the above embodiments associated with medical images, scrolling techniques coupled with the region(s) pertaining to the patient medical condition data could be used individually or in combination based on radiologist preference or by medical facility best practices. For example, the scrolling could be paused and an arrow shown to indicate a region pertaining to the patient medical condition data.

BRIEF DESCRIPTION OF FIGURES

FIG. 2 illustrates prior art showing scroll rates.

FIG. 5 illustrates a description of the user-controlled refresh rate including input methods and what the input methods accomplish.

FIG. 6 illustrates a description of the user-controlled viewing parameters including input methods and what the input methods accomplish.

FIG. 7 illustrates a description of the user-controlled reporting parameters including input methods and what the input methods accomplish.

FIG. 8 illustrates an example list of triggering events.

FIG. 9 illustrates a chart showing the three categories of predetermined responses.

FIG. 10 illustrates a list of the predetermined responses category #1, which is the timer-dependent image refresh rate.

FIG. 11 illustrates a list of the predetermined responses category #1, which is the timer-dependent image refresh rate.

FIG. 12 illustrates a list of the predetermined responses category #1, which is the timer-dependent image refresh rate.

FIG. 13 illustrates a list of the predetermined responses category #2, which is the image-dependent viewing parameter.

FIG. 14 illustrates an example list of the predetermined responses category #2, which is the image-dependent viewing parameter.

FIG. 15 illustrates an example list of the predetermined responses category #2, which is the image-dependent viewing parameter.

FIG. 16 illustrates an example list of the predetermined responses category #2, which is the image-dependent viewing parameter.

FIG. 17 illustrates an example list of the predetermined responses category #3, which is the image-dependent reporting parameter.

FIG. 18 illustrates an example list of the predetermined responses category #3, which is the image-dependent reporting parameter.

FIG. 19 illustrates an example of triggering events matched to the predetermined response of timer-dependent image refresh rate.

FIG. 22 illustrates the new scrolling technique implemented in this patent.

FIG. 23A illustrates an the integration of multiple factors to determine the optimum amount of time spent on each slice.

FIG. 23B illustrates application of the algorithm to a first example slice #300, which corresponds to the second row of the table in FIG. 23A.

FIG. 23C illustrates application of the algorithm to a first example slice #270, which corresponds to the third row of the table in FIG. 23A.

FIG. 23D illustrates application of the algorithm to a first example slice #150, which corresponds to the fourth row of the table in FIG. 23A.

FIG. 25A illustrates a slice of (e.g., slice N within the sequence) a set of medical images which is displayed for a duration of 0.25 seconds (note: this particular slice is not linked to a triggering event to cause a predetermined response of a slowing or speeding of the timer-dependent image refresh rate).

FIG. 25B illustrates a slice of (e.g., slice N+1 within the sequence) a set of medical images which is displayed for a duration of 0.25 seconds (note: this particular slice is not linked to a triggering event to cause a predetermined response of a slowing or speeding of the timer-dependent image refresh rate).

FIG. 25C illustrates a slice of (e.g., slice N+2 within the sequence) a set of medical images which is displayed for a duration of 3.5 seconds (note: this particular slice is linked to a triggering event to cause a predetermined response of a slowing of the timer-dependent image refresh rate).

FIG. 25D illustrates a slice of (e.g., slice N+3 within the sequence) a set of medical images which is displayed for a duration of 3.5 seconds (note: this particular slice is linked to a triggering event to cause a predetermined response of a slowing of the timer-dependent image refresh rate).

FIG. 25E illustrates a slice of (e.g., slice N+4 within the sequence) a set of medical images which is displayed for a duration of 0.25 seconds (note: this particular slice is not linked to a triggering event to cause a predetermined response of a slowing or speeding of the timer-dependent image refresh rate).

FIG. 25F illustrates a slice of (e.g., slice N+5 within the sequence) a set of medical images which is displayed for a duration of 0.25 seconds (note: this particular slice is not linked to a triggering event to cause a predetermined response of a slowing or speeding of the timer-dependent image refresh rate).

FIG. 29A illustrates example applications of image-dependent viewing parameters for advanced viewing on extended reality displays.

FIG. 29B illustrates an example left eye view of a breast cancer within that has undergone the segmentation process with the majority of non-breast cancer matter subtracted through a filtration process.

FIG. 29C illustrates an example right eye view of a breast cancer within that has undergone the segmentation process with the majority of non-breast cancer matter subtracted through a filtration process.

FIG. 29D illustrates an example left eye view of a breast cancer within that has undergone the segmentation process with the majority of non-breast cancer matter subtracted through a filtration process with the viewing position zoomed inward closer to the breast cancer, as compared to the viewing position from FIG. 29B.

FIG. 29E illustrates an example right eye view of a breast cancer within that has undergone the segmentation process with the majority of non-breast cancer matter subtracted through a filtration process with the viewing position zoomed inward closer to the breast cancer, as compared to the viewing position from FIG. 29C.

FIG. 32A illustrates a flow chart showing the triggering event criteria and the matched predetermined response of a timer-dependent image refresh rate.

FIG. 32B illustrates application of the triggering event criteria and the matched predetermined response of a timer-dependent image refresh rate in FIG. 32A.

FIG. 33 illustrates the integration of triggering events, timer-dependent image refresh rate, image-dependent viewing parameter, and image-dependent reporting parameter utilization into the interpretation of a chest x-ray.

DETAILED DESCRIPTION OF FIGURES

FIG. 1A Illustrates prior art wherein the left index finger at the top of the mouse roller wheel moving the mouse roller wheel toward the user with the right index finger at the bottom of the mouse roller wheel just lifting off of the mouse roller wheel at time point #1. 100 illustrates the mouse. 101 illustrates the left mouse button. 102 illustrates the right mouse button. 103 illustrates the mouse roller wheel. 104 illustrates the left hand with the left index finger at the top of the mouse roller wheel moving the mouse roller wheel 103 toward the user. 105 illustrates the right index finger at the bottom of the mouse roller wheel 103 just lifting off of the mouse roller wheel 103. This illustration represents a first time point.

FIG. 1B Illustrates prior art wherein the left index finger at the bottom of the mouse roller wheel and just lifting off of the mouse roller wheel with the right index finger at the top of the mouse roller wheel moving the mouse roller wheel toward the user at time point #2. 100 illustrates the mouse. 101 illustrates the left mouse button. 102 illustrates the right mouse button. 103 illustrates the mouse roller wheel. 106 illustrates the left hand with the left index finger at the bottom of the mouse roller wheel just lifting off of the mouse roller wheel 103. 107 illustrates the right index finger at the top of the mouse roller wheel 103 moving the mouse roller wheel 103 toward the user. This illustration represents a second time point. Note that the first time point and second time point both show snapshots in time of the mouse roller wheel 103 moving toward the user. This serves to generate a faster scrolling technique and speeds imaging interpretation. Time is not lost, as it would be using only a single finger, having completed one scroll to move the finger to the top of the roller ball and re-commence scrolling.

Figure 1:
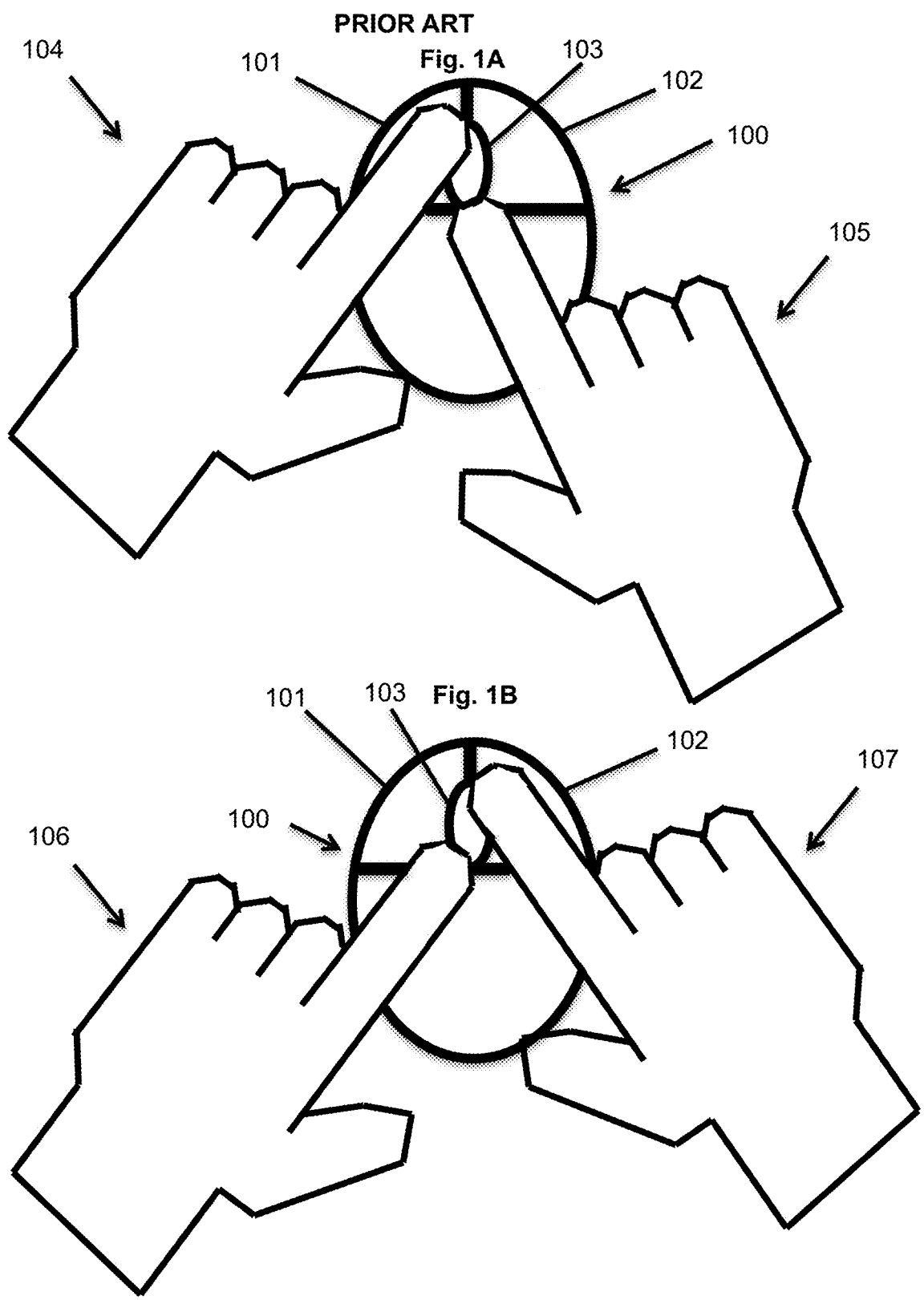
FIG. 1A Illustrates prior art wherein the left index finger at the top of the mouse roller wheel moving the mouse roller wheel toward the user with the right index finger at the bottom of the mouse roller wheel just lifting off of the mouse roller wheel at time point #1.
FIG. 1B Illustrates prior art wherein the left index finger at the bottom of the mouse roller wheel and just lifting off of the mouse roller wheel with the right index finger at the top of the mouse roller wheel moving the mouse roller wheel toward the user at time point #2.

FIG. 2 illustrates prior art showing scroll rates. There are two current methods for scrolling. The first method is the scroll wheel as shown in FIG. 1 wherein the radiologist uses a single finger or both fingers to move from slice to slice. The second method is by holding down the arrow key. A radiologist was asked on a standard Radiology Picture Archiving Communication System (PACS) to hold the down arrow key and see how long it took for all images to be displayed. In this example, the radiologist reviewed a stack of 512 slices. It took 83 seconds of holding the down arrow key to go through all 512 slices. This is equivalent to 0.16 seconds per slice. All slices are shown for the exact same amount of time.

Figure 3:
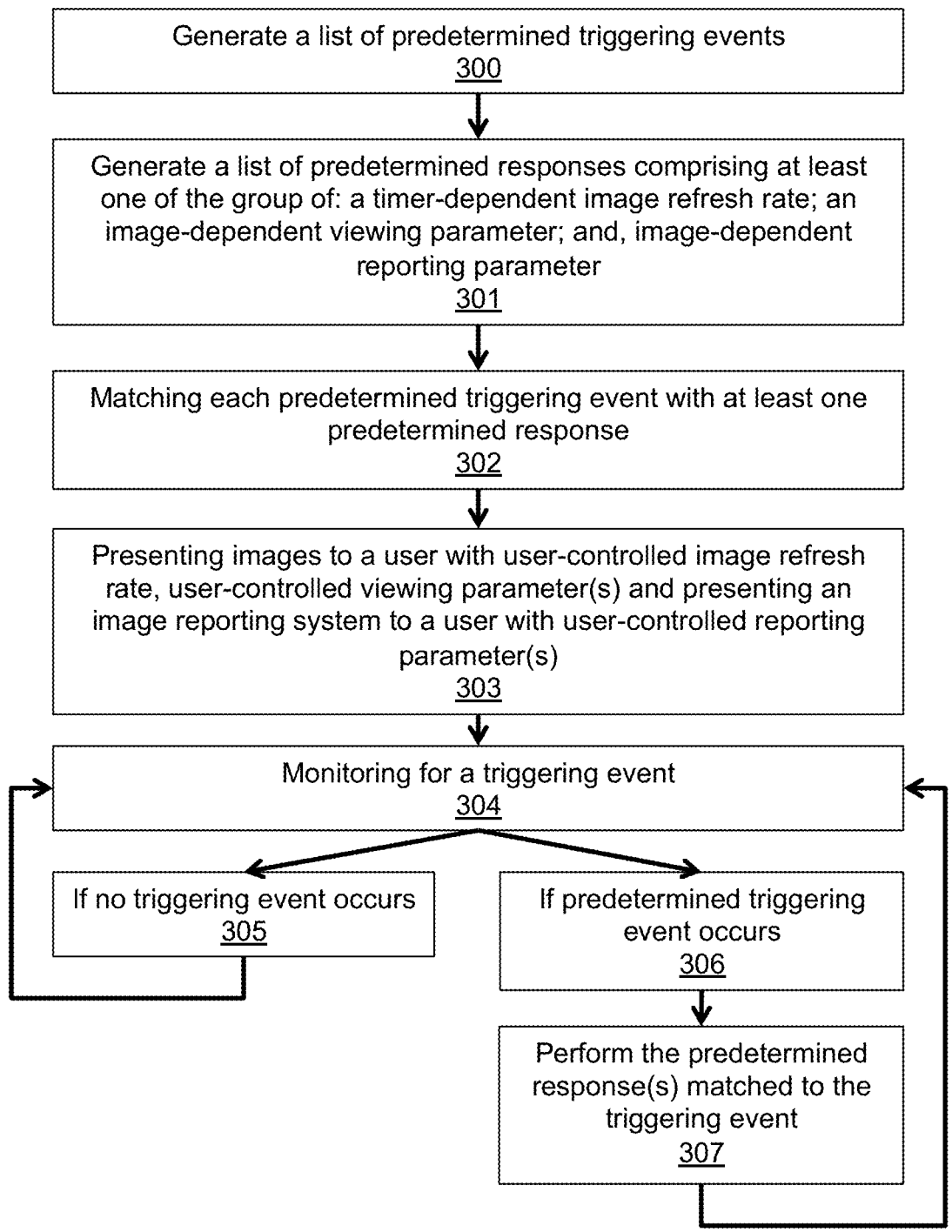
FIG. 3 illustrates a processing diagram for the key steps in this patent.

FIG. 3 illustrates a processing diagram for the key steps in this patent. Step 300 illustrates generating a list of predetermined triggering events. Step 301 illustrates generate a list of predetermined responses comprising at least one of the group of: a timer-dependent image refresh rate; an image-dependent viewing parameter; and, image-dependent reporting parameter. Step 302 illustrates matching each triggering event with at least one predetermined response. Step 303 illustrates presenting images to a user with user-controlled image refresh rate, user-controlled viewing parameter(s) and presenting an image reporting system to a user with user-controlled reporting parameter(s). Step 304 illustrates monitoring for a triggering event. Step 305 illustrates a time step wherein no triggering event occurs wherein the next processing step is to return to step 304 wherein monitoring for a triggering event is performed. Step 306 illustrates a time step wherein a predetermined triggering event occurs. Step 307 illustrates performing the predetermined image adjustment(s) matched to the triggering event. Upon completing the predetermined image adjustment(s) from step 307, the next processing step is to return to step 304 and continue monitoring for a triggering event.

Figure 4:
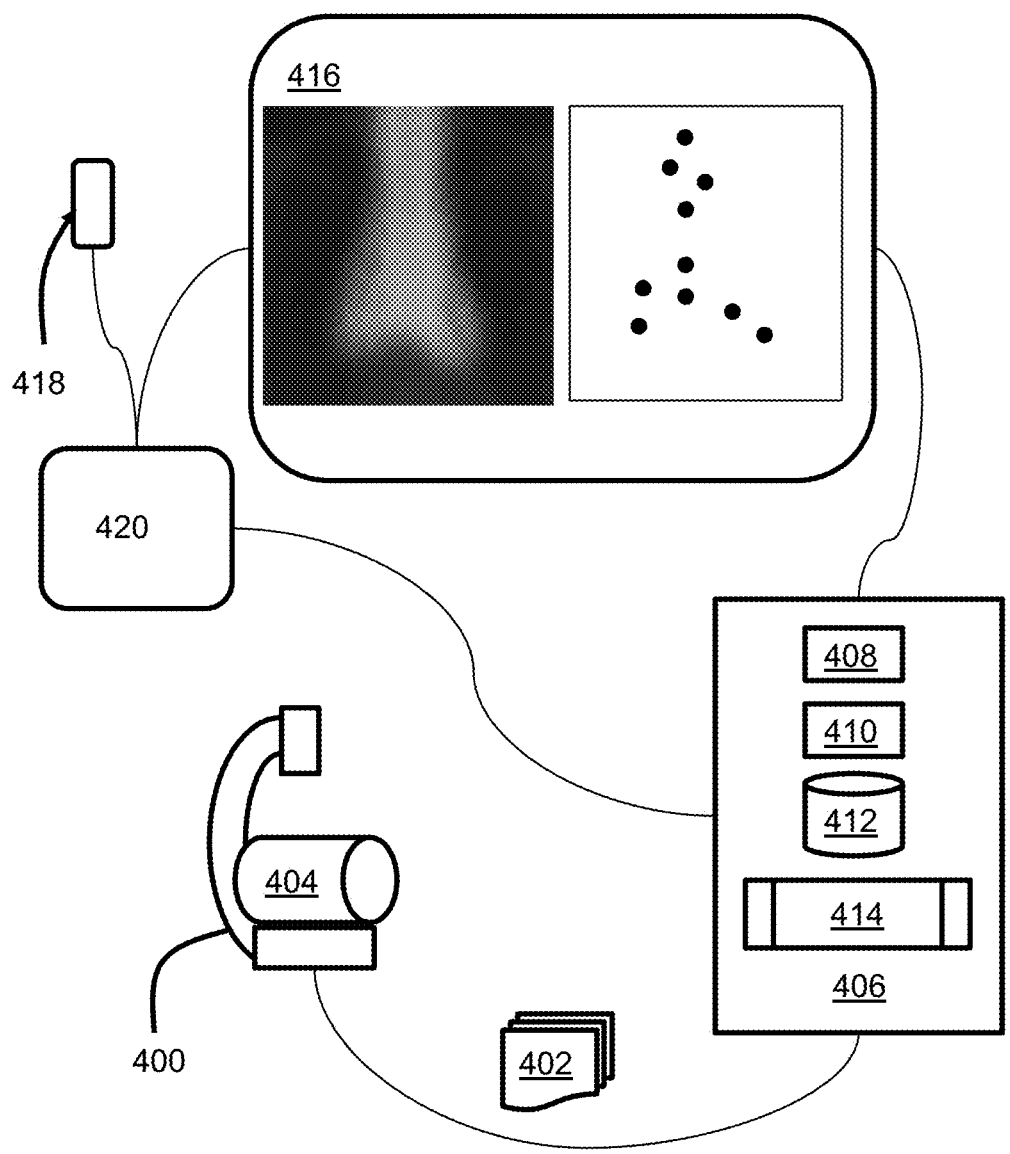
FIG. 4 illustrates an apparatus for implementing the process illustrated in FIG. 3.

FIG. 4 illustrates an apparatus for implementing the process illustrated in FIG. 3. A radiologic imaging system 400 (e.g., X-ray, ultrasound, CT (computed Tomography), PET (Positron Emission Tomography), or MM (Magnetic Resonance Imaging)) is used to generate 2D medical images 402 of an anatomic structure 404 of interest. The medical images 402 are provided to an image processor 406, that includes processors 408 (e.g., CPUs and GPUs), volatile memory 410 (e.g., RAM), and non-volatile storage 412 (e.g. HDDs and SSDs). A program 414 running on the image processor implements one or more of the steps described in FIG. 3. Processed images are generated from the medical images and displayed on an IO device 416. The IO device 416 may include a virtual reality headset, mixed reality headset, augmented reality headset, monitor, tablet computer, PDA (personal digital assistant), mobile phone, or any of a wide variety of devices, either alone or in combination. The IO device 416 may include a touchscreen, and may accept input from external devices (represented by 418) such as a keyboard, mouse, and any of a wide variety of equipment for receiving various inputs. However, some or all the inputs could be automated, e.g. by the program 414. Finally, as discussed further in FIG. 3 and the rest of this patent, a series of processing strategies 420 are implemented, which facilitate viewing of medical images by medical personnel.

FIG. 5 illustrates a description of the user-controlled refresh rate including input methods and what the input methods accomplish. 500 illustrates an overview of the user-controlled refresh rate. User inputs include, but are not limited to, the following: a user-performed finger movement on a rollerball on the mouse; a user-performed finger movement on a scroll wheel on a mouse; a user-performed click and drag movement on a mouse; and, a user-performed finger strike of an arrow key on a keyboard. What the user inputs accomplish include, but are not limited to, the following: user-desired movement of a single step (e.g. from a first slice to a second slice); user-desired movement of multiple steps (e.g., from a first slice to a second slice to a third slice); user-desired movement in the forward or reverse direction (e.g., superior to inferior, inferior to superior, etc.); user-desired movement of at a fast rate (e.g., two finger scrolling technique on scroll wheel on mouse); user-desired movement of at a slow rate (e.g., single finger scrolling technique on scroll wheel on mouse).

FIG. 6 illustrates a description of the user-controlled viewing parameter including input methods and what the input methods accomplish. 600 illustrates an overview of the user-controlled viewing parameter. User inputs include, but are not limited to, the following: a user-performed strike of a hotkey on a keyboard; a user-performed click and drag movement on a mouse; a user-performed movement of a scroll wheel on a mouse; and, a user-performed point and click on a drop down menu. What the user inputs accomplish include, but are not limited to, the following: a user-desired window and level setting; a user-desired false color setting; a user-desired zoom setting; a user-desired image rotation position; a user-desired convergence point; and, a user-desired viewing angle setting.

FIG. 7 illustrates a description of the user-controlled reporting parameters including input methods and what the input methods accomplish. 700 illustrates an overview of the user-controlled reporting parameter. User inputs include, but are not limited to, the following: a user-performed strike of a button on a microphone; a user-performed strike of a hotkey on a keyboard; a user-performed click and drag movement on a mouse; a user-performed movement of a scroll wheel on a mouse; and, a user-performed point and click on a drop down menu. What the user inputs accomplish include, but are not limited to, the following: a user-desired input of text; a user-desired alteration of text; a user-desired deletion of text; and, a user-desired navigation from a first section of a report to a second section of a report.

FIG. 8 illustrates an example list of triggering events. 800 illustrates the list of triggering events. The list of triggering events include, but are not limited to, the following: imaging findings; imaging metadata; user eye tracking data; user facial recognition data; and, combination thereof.

With respect to imaging findings, a first example are findings categorized by AI (e.g., AI algorithm determines CT head scan is abnormal showing an intracranial hemorrhage, AI algorithm determines that a head CT scan is normal, etc.).

A second example include findings of a segmented structure. Some small structures are very important in the human body and other small structures are not as important clinically. One such structure that is important is the pituitary stalk. This is a thin structure connecting the pituitary gland to the hypothalamus. This structure has a disproportionate amount of pathology and therefore deserves a disproportionate amount of attention by a radiologist. Therefore, when the pituitary stalk appears on the image, this appearance event is an example of a triggering event.

Another example is the property of a structure being reviewed. It is easier to hide a subtle finding in a complex scene, such as finding Waldo in the child's game Where's Waldo. Waldo can be easily be hidden because the scene is so complex. Therefore, the complexity of the scene can serve as a triggering event (e.g., highly complex, heterogeous scenes can cause a triggering event). Additionally, some slices may contain several important structures (e.g., coronal image through the sella and pituitary stalk and cavernous sinuses), which can also serve as a triggering event.

Another example is the checklist item being reviewed. For example, the radiologist may prefer to use a standard window and level setting for the abdomen. Then, after the last checklist item is reviewed using the standard window and level setting for the abdomen, the radiologist may elect to move to the bone items on the checklist. The action of moving to the next item on the checklist itself can act as a triggering event.

Additionally, if an abnormality was identified on a prior imaging examination and if the equivalent slice on the current imaging examination could be determined through localization, then the event of an abnormality on a prior imaging examination could be used as a triggering event.

Next, metadata associated with the imaging examination can also be used as a triggering event. A first example is patient history relevant to a particular structure being imaged. For example, if the patient's medical record showed a history of kidney disease and elevated creatinine, then this metadata can serve as a triggering event. The preferred embodiment would be for metadata to be a component of a triggering event, rather than in isolation. For example, a dual triggering event would occur when both of the following occur: first, a history of kidney disease is identified in the patient's medical record; and, second, the kidney is within the active item being reviewed by the radiologist. Next, user eye tracking metrics can serve as a triggering event. For example, the user can also perform zooming and panning on his own and eye tracking performed in accordance with methods disclosed in U.S. Patent Application 62/985,363. When coupled with segmentation, metrics such as number of fixation points within a certain distance within a segmented structure can be accomplished. To continue the pituitary stalk example and apply it to the eye tracking, a triggering event could be that a minimum of 5 seconds and 10 fixation points need to be performed on each imaging slice containing the pituitary stalk. A triggering event could occur once these metrics are achieved. Next, user facial expression recognition metrics can be performed. For example, metrics relating to attentiveness is an example of a triggering event.

Predetermined response criteria (timer-dependent image refresh rate, image-dependent viewing parameter, image-dependent reporting parameter) can also act as a triggering event. For example, a timer-dependent image refresh rate can act as a triggering event and cause an image-dependent viewing parameter to occur. Alternatively, a timer-dependent image refresh rate can act as a triggering event and cause an image-dependent viewing parameter to occur. Finally, any of the above can be put together as a triggering event.

FIG. 9 illustrates a chart showing the three categories of predetermined responses. 900 illustrates the text box. The first category of predetermined response the timer-dependent image refresh rate. The second category is the image-dependent viewing parameter. The third category is the image-dependent reporting parameter. Each of these will be taught in detail in subsequent figures.

FIG. 10 illustrates a list of the predetermined responses category #1, which is the timer-dependent image refresh rate. This is the first of three figures to each this method. 1000 illustrates a text box with three types of timer-dependent image refresh rates.

The first timer-dependent image refresh rate causes a pause at a single image for a minimum period of time. For example, assume the user controlled scrolling rate is to see each image for 0.16 seconds per slice. The timer-dependent refresh rate when triggered causes a pause of 1.00 seconds. After this minimum period of time has passed, the refresh rate the user-controlled refresh rate (0.16 seconds per slice) resumes. This is useful by forcing the user to slow down on when triggering event (e.g., triggering event is the detection by an AI algorithm of a small pulmonary nodule on only a single slice), which could otherwise easily be missed by a user. Thus, a triggering event has caused the predetermined response of the timer-dependent image refresh rate to pause at a single image for a minimum period of time.

The second timer-dependent image refresh rate utilized for at least two consecutive images wherein the timer-dependent image refresh rate is slower than the user-controlled refresh rate. For example, assume the user controlled scrolling rate is to see each image for 0.16 seconds per slice. The timer-dependent refresh rate when triggered causes a pause of 1.00 seconds on two consecutive slices. After the 1.00 second pause on the first slice, the second slice is displayed. After the 1.00 second pause on the second slice, the user-controlled refresh rate (0.16 seconds per slice) resumes for the third slice and onward. This is useful by forcing the user to slow down on an important finding (e.g., triggering event is the detection by an AI algorithm of a small pulmonary nodule on two slices), which could otherwise easily be missed by a user. Thus, a triggering event has caused the predetermined response of the timer-dependent image refresh rate to be utilized for at least two consecutive images wherein the timer-dependent image refresh rate is slower than the user-controlled refresh rate.

The third timer-dependent image refresh rate utilized for at least two consecutive images wherein the timer-dependent image refresh rate is faster than the user-controlled refresh rate. For example, assume the user controlled scrolling rate is to see each image for 0.16 seconds per slice. The timer-dependent refresh rate when triggered causes a pause of 0.01 seconds on two consecutive slices. After the 0.01 second pause on the first slice, the second slice is displayed. After the 0.01 second pause on the second slice, the user-controlled refresh rate (0.16 seconds per slice) resumes. This is useful by forcing the user to speed up on an non-important data (e.g., triggering event is the detection by an AI algorithm of an air gap above the patients head on a head CT scan). This contains no data and the radiologist need not spend valuable seconds while scrolling through the air gap above the head until he/she reaches the scalp. Thus, a triggering event has caused the predetermined response of the timer-dependent image refresh rate to be utilized for at least two consecutive images wherein the timer-dependent image refresh rate is faster than the user-controlled refresh rate.

FIG. 11 illustrates a list of the predetermined responses category #1, which is the timer-dependent image refresh rate. This is the second of four figures to each this method. 1100 illustrates a text box with two types of timer-dependent image refresh rates.

The fourth timer-dependent image refresh rate utilized only a limited number of times, such that after the limited number of times is exceeded, the refresh rate is user-controlled. For example, first, assume the user controlled scrolling rate is to see each image for 0.16 seconds per slice. The timer-dependent refresh rate when a triggering event causes a pause of 1.00 seconds. After this minimum period of time has passed, the refresh rate the user-controlled refresh rate (0.16 seconds per slice) resumes. Next, assume that the user scrolls back over the same slice that triggering event causes a pause of 1.00 seconds. An option at this juncture is to no longer require the 1.00 second delay, so that the second time the slice is presented, it is shown for 0.16 seconds (not 1.00 seconds). This is useful by forcing the user to slow down on an important finding (e.g., triggering event is the detection by an AI algorithm of a small pulmonary nodule on only a single slice), which could otherwise easily be missed by a user. Once the user characterizes it, it would be useful to have the option to no longer require the 1.00 second delay so as to speed interpretation. Thus, a triggering event has caused the predetermined response of the timer-dependent image refresh rate to be utilized only a limited number of times as described.

The fifth timer-dependent image refresh rate is variable wherein a first image refresh rate is utilized when a first set of images are first presented and wherein a second image refresh rate is utilized when the first set of images are second presented. For example, first, assume the user controlled scrolling rate is to see each image for 0.16 seconds per slice. The timer-dependent refresh rate when triggered causes a pause of 1.00 seconds. After this minimum period of time has passed, the refresh rate the user-controlled refresh rate (0.16 seconds per slice) resumes. Next, assume that the user scrolls back over the same slice that triggered a pause of 1.00 seconds. An option at this juncture is to reduce the length of the delay to somewhere in between 0.16 seconds and 1.00 seconds. This is useful by forcing the user to slow down on an important finding (e.g., triggering event is the detection by an AI algorithm of a small pulmonary nodule on only a single slice), which could otherwise easily be missed by a user. Once the user characterizes it, it would be useful to have a shorter period of time where the image was displayed (e.g., between 0.16 seconds and 1.00 seconds) so as to speed interpretation. Thus, a triggering event has caused the predetermined response of the timer-dependent image refresh rate to be variable as described.

FIG. 12 illustrates a list of the predetermined responses category #1, which is the timer-dependent image refresh rate. 1200 illustrates a text box. This is the third of three figures to each this method. 1200 illustrates a text box with four a timer-dependent image refresh rates. The sixth timer-dependent refresh rate is user-dependent wherein a first set of images is presented to a first user at a first timer-dependent image refresh rate and the first set of images is presented to a second user at a second timer-dependent image refresh rate. For example, assume that there are two different users. User #1 has a first preference. User #2 has a second preference. The first preference and second preference are different. User #1 sets a first preference for a 1.00 second delay each time a certain triggering event occurs (e.g., triggering event is the detection by an AI algorithm of a small pulmonary nodule on only a single slice), which could otherwise easily be missed by a user. User #2 sets a different preference setting as compared to user #1. For example, User #2 sets a 1.50 second delay each time the same triggering event occurs (e.g., triggering event is the detection by an AI algorithm of a small pulmonary nodule on only a single slice), which could otherwise easily be missed by a user. This is useful because different users may have different abilities or personal preferences. Additionally, the same user could choose to the timer-dependent refresh rates for a variety of other reasons, such as the time of the day. Thus, a triggering event has caused the predetermined response of the timer-dependent image refresh rate to be user-dependent as described.

The seventh timer-dependent refresh rate is independent of the user-inputted image refresh rate and occurs over at least two consecutive images. First, assume that a user wants to do a hands off approach and is therefore not scrolling and also assume that some of the slices are tied to triggering events and some of the slices are not tied to triggering events. This is discussed in detail in FIG. 22. This is useful because different users may have different preferences. Additionally, the same user could choose to the timer-dependent refresh rates for a variety of other reasons or allow the timer-dependent refresh rate to be determined by an AI algorithm. Thus, a triggering event has caused the predetermined response of the timer-dependent image refresh rate to be independent of user-inputted image refresh rate.

FIG. 13 illustrates a list of the predetermined responses category #2, which is the image-dependent viewing parameter. 1300 illustrates a text box.

The first image-dependent viewing parameter of performing conventional windowing and leveling for the entire dataset. First, assume the radiologist has applied a first window and level setting to the entire CT abdomen and pelvis dataset. Assume that the radiologist has completed all checklist items that required the first window and level setting and is now moving to a subsequent item on the checklist that requires a second window and level setting. The triggering event (e.g., moving to a item on the checklist linked (e.g., see processing block 302 in FIG. 3) to a preferred window and level setting different from the current window and level setting) has caused the predetermined response of the image dependent viewing parameter of performing conventional windowing and leveling for the entire dataset. For example, after the last checklist item is reviewed using the standard window and level setting for the abdomen, the radiologist may elect to move to the bone items on the checklist. The action of moving to the next item on the checklist itself can act as a triggering event. This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling. Thus, a triggering event has caused the predetermined response of the image-dependent viewing parameter to perform conventional windowing and leveling for the entire dataset.

The second image-dependent viewing parameter of setting a window and level parameter for a first image slice independently from a window and level parameter for a second image slice. First, assume that the radiologist is scrolling through the liver with a standard liver window and level setting. Assume that there an triggering event (e.g., a mass lesion in the liver discovered by an AI algorithm with similar Hounsfield Units to normal liver parenchyma). This is useful because it instantly provides an improved visual analysis of the mass lesion identified by the AI algorithm and saves the step of detection, saves the step of mentally deciding whether to window and level, saves the step of user-performed striking a hotkey, saves the step of mouse click and drag for windowing and leveling. Thus, a triggering event has caused the predetermined response of the image-dependent viewing parameter to set a window and level parameter for a first image slice independently from a window and level parameter for a second image slice.

FIG. 14 illustrates an example list of the predetermined responses category #2, which is the image-dependent viewing parameter. 1400 illustrates a text box.

The third image-dependent viewing parameter includes displaying simultaneously a first visual representation adjustment logic for a first segmented structure and a second visual representation adjustment logic for a second segmented structure wherein the first visual representation adjustment logic is different from the second visual representation adjustment logic. First, assume the radiologist now moving to the pancreas, which is notoriously a difficult region to identify pathology because the pathologic lesion is commonly only a few Hounsfield Units different from normal pancreas tissue. The triggering event (e.g., moving to a item on the pancreas checklist item) has caused the predetermined response of the image dependent viewing parameter of performing dual windowing and leveling, as disclosed in U.S. Pat. No. 10,584,400. For example, after the spleen checklist item is reviewed using the standard window and level setting for the abdomen, the radiologist may elect to move to the pancreas on the checklist. The action of moving to the next item on the checklist itself can act as a triggering event. This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling. Thus, a triggering event has caused the predetermined response of the image-dependent viewing parameter to perform dual windowing and leveling for the pancreas.

The fourth image-dependent viewing parameter is a false color setting. First, assume the radiologist is viewing volume rendered images on a 2D monitor. Assume that the radiologist prefers a color schematic wherein the blood vessels are light pink colored when they are not actively being examined (e.g., such as when the radiologist is reviewing the bones), but appear bright red when actively being examined. The triggering event is the action of moving from the bones item on the checklist to the blood vessel item on the checklist. The predetermined response of the image dependent viewing parameter is the implementation of red false color of the blood vessels. This is useful because it instantly provides an improved visual analysis of the next item on the checklist and saves the step of user mentally deciding what the preferred window and level setting is, saves the step of user-performed striking a hotkey, saves the step of mouse click and drag for windowing and leveling. Thus, a triggering event has caused the predetermined response of the image-dependent viewing parameter to perform false color.

FIG. 15 illustrates an example list of the predetermined responses category #2, which is the image-dependent viewing parameter. 1500 is a text box.

The fifth image-dependent viewing parameter of performing zooming. First, assume the radiologist is viewing a stack of CT slices through the lungs and a triggering event (e.g., a small 5 mm pulmonary nodule detected by an AI algorithm on the image slice) occurs. This small pulmonary nodule is seen by the radiologist in an un-zoomed image, but the radiologist needs to zoom in to better characterize it. In this example, the triggering event of the small pulmonary nodule appearing on the screen causes the predetermined response of an image-dependent viewing parameter of performing the action of zooming. This is useful because it instantly provides an improved visual analysis of the small finding and saves the step of detection, saves the step of mentally deciding whether to zoom, saves the step of user-performed striking a hotkey, saves the step of mouse click and drag. Thus, a triggering event has caused the predetermined response of the image-dependent viewing parameter to perform zooming.

The sixth image-dependent viewing parameter is an image rotation. First, assume a triggering event (e.g., a small fracture of the posterior malleolus of the tibia enters the field of view on an axial slice). This small fracture is seen by the radiologist, but the radiologist needs to better characterize it with a volume rendered image. In this example, the triggering event causes the predetermined response of an image-dependent viewing parameter of performing the action of generating a side panel on the radiology monitor with a volume rendered image of the posterior malleolus with a rotation. Additional options include automatic image markup with annotations (e.g., arrow, circle). This is useful because it instantly provides an improved visual analysis of the small finding and saves the step of detection, saves the step of mentally deciding whether to create volume rendered images, saves the step of user-performed striking a hotkey, saves the step of mouse click and drag to rotate. Thus, a triggering event has caused the predetermined response of the image-dependent viewing parameter to perform image rotation.

FIG. 16 illustrates an example list of the predetermined responses category #2, which is the image-dependent viewing parameter. 1600 is a text box. The seventh image-dependent viewing parameter is a viewing angle setting. First, assume a triggering event (e.g., a small fracture of the posterior malleolus of the tibia enters the field of view on an axial slice). This small fracture is seen by the radiologist, but the radiologist needs to better characterize it with a volume rendered image. In this example, the triggering event causes the predetermined response of an image-dependent viewing parameter of performing the action of generating a side panel on the radiology monitor with a volume rendered image of the posterior malleolus with six viewing positions (from top, from bottom, from left, from right, from front, from back), all of which have viewing angles directed toward the fracture. This is useful because it instantly provides an improved visual analysis of the small finding and saves the step of detection, saves the step of mentally deciding whether to create volume rendered images, saves the step of user-performed striking a hotkey, saves the step of mouse click and drag to rotate. Thus, a triggering event has caused the predetermined response of the image-dependent viewing parameter to generate viewing angles.

The eighth image-dependent viewing parameter includes advanced image processing techniques. First, assume a radiologist is viewing contiguous cross-sectional imaging slices and a triggering event (e.g., detection by an AI algorithm of a small pulmonary nodule on only a single slice) occurs. This small nodule is seen by the radiologist, but the radiologist needs to better characterize it with advanced image processing techniques. In this example, the triggering event causes the predetermined response of at least one of the group of: viewing on an extended reality display; 3D cursor usage (see U.S. patent application Ser. No. 15/878,463; virtual tool usage (see PCT/US19/47891); voxel manipulation (see U.S. patent application Ser. No. 16/195,251); and, incorporating data unit assurance markers (see U.S. patent application Ser. No. 16/785,506). This is useful because it instantly provides an improved visual analysis of the small finding and saves the step of detection, saves the step of mentally deciding whether to create volume rendered images, saves the step of user-performed striking a hotkey, saves the step of mouse click and drag to rotate. Thus, a triggering event has caused the predetermined response of the image-dependent viewing parameter to generate advanced image processing techniques.

FIG. 17 illustrates an example list of the predetermined responses category #3, which is the image-dependent reporting parameter. 1700 is a text box.

The first image-dependent reporting parameter wherein text is automatically inputted into a section of a report. First, assume a radiologist is viewing contiguous axial cross-sectional imaging slices and a triggering event (e.g., detection by an AI algorithm of a pulmonary nodule in the right lung that measures 5 mm in greatest axial dimension) occurs. In this example, the triggering event causes the predetermined response of an image-dependent reporting parameter of performing the action of entering text stating "5 mm right lung pulmonary nodule". This is useful because it saves time of entering report text and also prevents any accidental omission (e.g., the radiologist intended to describe the pulmonary nodule, but perhaps got distracted from a phone call and therefore never inserted the text describing the pulmonary nodule into the report). Thus, a triggering event has caused the predetermined response of the image-dependent reporting parameter to insert text into the radiology report.

The second image-dependent reporting parameter wherein text in a section of a report is automatically altered. Next, consider continuing with the example above wherein the text stating "5 mm right lung pulmonary nodule". Consider now, that viewing is of contiguous coronal imaging slices and a triggering event (e.g., detection by an AI algorithm of the same pulmonary nodule in the right lung as above, but it measures 7 mm in greatest coronal dimension) occurs. In this example, the triggering event causes the predetermined response of an image-dependent reporting parameter of performing the action of automatically altering text to state "7 mm right lung pulmonary nodule", not "5 mm right lung pulmonary nodule". This is useful because it saves time of altering report text and also prevents any accidental omission (e.g., the radiologist intended to alter the size of the pulmonary nodule, but perhaps got distracted from a phone call and therefore never inserted the text describing the pulmonary nodule into the report). Thus, a triggering event has caused the predetermined response of the image-dependent reporting parameter to alter text into the radiology report.

FIG. 18 illustrates an example list of the predetermined responses category #3, which is the image-dependent reporting parameter. 1800 is a text box.

The third image-dependent reporting parameter wherein text in a section of a report is automatically deleted. First, assume a radiologist is viewing contiguous axial cross-sectional imaging slices of the femur and a triggering event (e.g., detection by an AI algorithm of a bone lucency determined to be 50% likely to represent a fracture and 50% likely to represent a nutrient foramen) occurs. In this example, the triggering event causes the predetermined response of an image-dependent reporting parameter of performing the action of entering text stating "lucency in femur, which may represent a fracture or nutrient foramen". Next, assume that the contiguous sagittal images are reviewed and a second triggering event occurs (e.g., detection by an AI algorithm of a bone lucency determined to be 100% likely to represent a fracture). In this example, the second triggering event causes the predetermined response of an image-dependent reporting parameter of performing the action of deleting text (i.e., lucency in femur, which may represent a fracture or nutrient foramen) such that the report now states "femur fracture"). This is useful because it saves time of deleting report text and also prevents any accidental inclusion of text that was not meant to make it to the report (e.g., the radiologist intended to describe the pulmonary nodule, but perhaps got distracted from a phone call and therefore never inserted the text describing the pulmonary nodule into the report). Thus, a triggering event has caused the predetermined response of the image-dependent reporting parameter to deleting text into the radiology report.

The fourth image-dependent reporting parameter wherein a cursor is automatically moved from a first section of a report to a second section of a report. First, assume a radiologist is viewing contiguous axial cross-sectional imaging slices of the abdomen and a triggering event (e.g., axial cross-sectional imaging slices include the kidney) occurs. In this example, the triggering event causes the predetermined response of an image-dependent reporting parameter of performing the action of moving the cursor from a first section of the report (e.g., adrenal gland section) to a second section of a report (e.g., kidney section). This is useful because it saves time of manually switching between sections. Thus, a triggering event has caused the predetermined response of the image-dependent reporting parameter to switch to a new section of the radiology report.

FIG. 19 illustrates an example of triggering events matched to the predetermined response of timer-dependent image refresh rate.

The size of the image can serve as a triggering event to determine the timer-dependent image refresh rate. First, assume that there are multiple slices of the breast. The slices have varying size. Consider a first slice of the breast located close to the nipple having breast tissue in a roughly circular region and measuring an approximate 2 cm in radius, such that the area of the breast tissue on this slice would be approximately 12.56 $cm^2$. Consider a second slice of the same breast located closer to the chest wall having breast tissue in a roughly circular region, but measuring 5 cm in radius, such that the area of the breast tissue on this slice would be approximately 78.50 $cm^2$. This slice therefore contains 6.25 times the number of pixels. Assume that the image refresh rate is adjusted such that it is slower for the area with the larger field of view. This is useful because the user, by using a smart scroll system, the amount of time on each image could be better allocated, wherein the smaller region has a smaller amount of time and the larger region has a larger amount of time. This therefore improves image analysis.

The complexity of the image can serve as a triggering event to determine the timer-dependent image refresh rate. First, assume that there are multiple slices of the breast. The slices have varying complexity. Consider a first slice of the breast containing homogenous fatty tissue. Consider a second slice of a different breast containing heterogeneous tissue with some areas of fat, some areas of calcification and some areas of glandular tissue. The second breast demonstrates higher amount of complexity of the scene as compared to the first breast. Assume that the image refresh rate is adjusted such that it is slower for the second more complex breast as compared to the first homogeneous breast. This is useful because the user, by using a smart image refresh rate system, the amount of time on each image could be better allocated, wherein the more homogeneous region has a smaller amount of time and the more heterogeneous region has a larger amount of time. This therefore improves image analysis.

The contrast between the background and the pathology can serve as a triggering event to determine the timer-dependent image refresh rate. First, assume that the area being examined is the pancreas and the purpose of the exam is to detect a pancreatic tumor, which is notoriously difficult to interpret because pancreatic cancer is of similar Hounsfield Units to normal pancreas tissue. This low image contrast resolution is taken into account when determining the timer-dependent refresh rate and causes the timer-dependent refresh rate to slow down. Second, assume that the area being examined is a diffusion weighted image of the brain and the purpose of the exam is to detect a stroke. Acute strokes show up as very bright white pixels whereas the background normal brain is mid-gray. This high contrast resolution is taken into account when determining the timer-dependent refresh rate and causes the timer-dependent refresh rate to speed up. This is useful because the user, by using a smart image refresh rate system, the amount of time on each image could be better allocated, wherein the more high contrast regions have a smaller amount of time allocated and the low contrast regions have a larger amount of time allocated. This therefore improves image analysis.

The probability of pathology in the image can serve as a triggering event to determine the timer-dependent image refresh rate. First, assume that the area being examined is the lungs in a 75 year old man who has a history of 100 pack years and emphysema. This patient is at high risk of lung cancer and the fact that the patient is at high risk of lung cancer is taken into account into the timer-dependent image refresh rate, which is slow. Second, assume that the area being examined is the lungs in a 10 year old child, which has a finite probability of harboring a lung cancer, albeit exceedingly rate. This exceedingly low probability of incidentally discovering lung cancer is taken into account into the timer-dependent image refresh rate, which is faster than the first example of the 75 year old man. This is useful because the user, by using a smart image refresh rate system, the amount of time on each image could be better allocated, wherein the low probability regions have a smaller amount of time allocated and the high probability regions have a larger amount of time allocated. This therefore improves image analysis.

The severity of pathology in the image can serve as a triggering event to determine the timer-dependent image refresh rate. Assume a patient with a history of lung cancer with widespread metastatic disease is being imaged. First, assume that the area being examined is the brain for metastatic disease, which is a very severe pathology and requires neurosurgical management. Thus, the timer-dependent image refresh rate should be slower when reviewing this severe finding. Second, assume that the area being examined is the vertebral body endplates for osteophytosis. In the grand scheme of things, this is a minor finding, as compared to the pressing issue of cancer staging and assessment for brain metastases. Thus, the timer-dependent image refresh rate should be faster when reviewing these relatively benign findings. This is useful because the user, by using a smart image refresh rate system, the amount of time on each image could be better allocated, wherein the areas with potentially severe pathology have a larger amount of time allocated and the areas with likely benign pathology have a larger amount of time allocated. This therefore improves image analysis.

The radiologist's personal characteristics can serve as a triggering event to determine the timer-dependent image refresh rate. The personal characteristic of age influences timer-dependent image refresh. Naturally, as one gets older or as one's eye sights becomes more limited, the timer-dependent image refresh rate slows down. Additionally, personal preference may slow down or speed up the timer-dependent image refresh rate. It is also important to factor in eye tracking data and facial recognition data into timer-dependent image refresh rate, which is discussed elsewhere throughout this patent.

External characteristics can serve as a triggering event to determine the timer-dependent image refresh rate. The time of the day can also influence timer-dependent image refresh. For example, on the very first case of the morning, the timer-dependent image refresh rate may be set to a slower speed. As one gets warmed up, the timer-dependent image refresh rate may be set to a higher speed.

Figure 20:
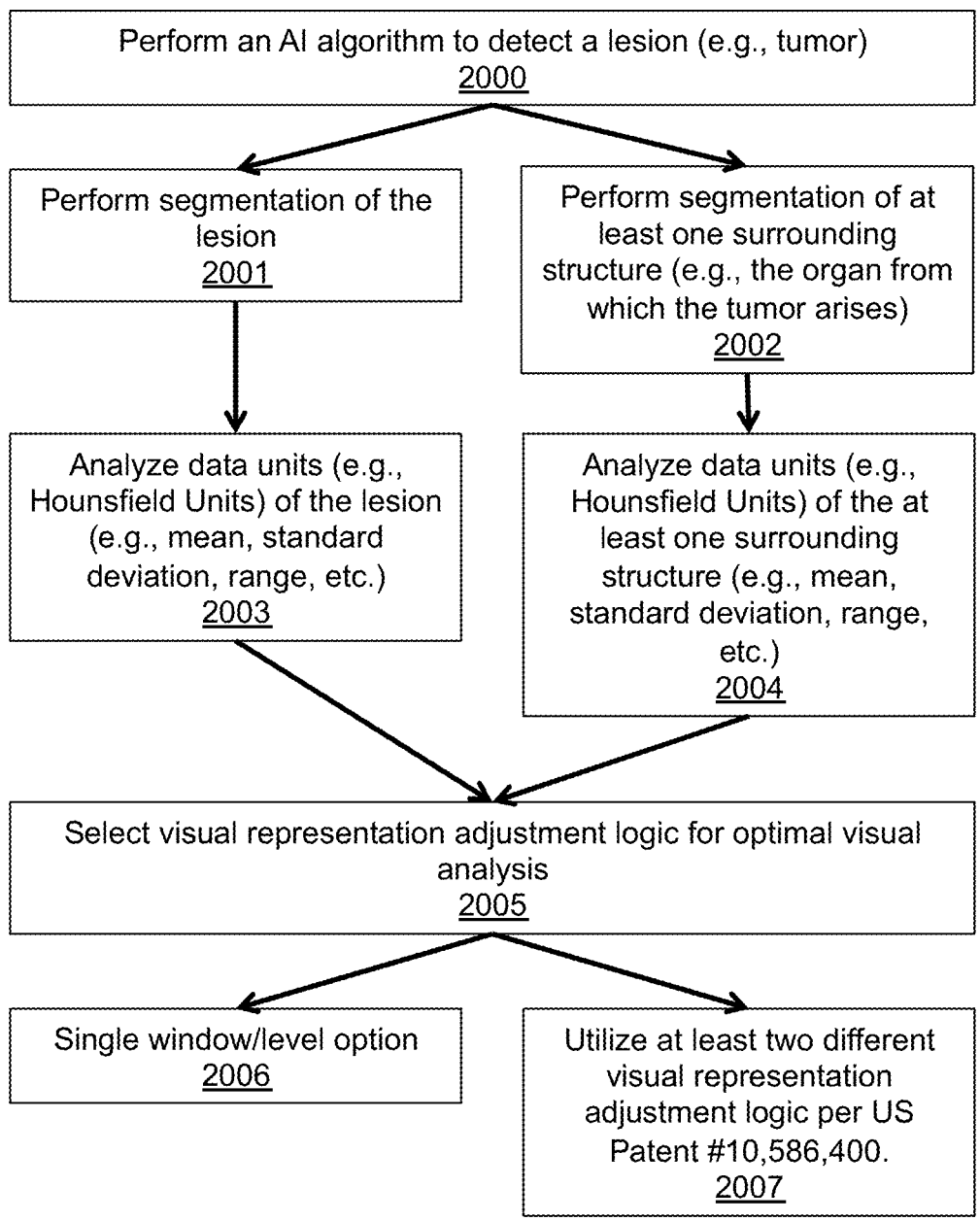
FIG. 20 illustrates a method of automatically performing window and level settings for improved viewing of a lesion detected by an AI algorithm.

FIG. 20 illustrates a method of automatically performing window and level settings for improved viewing of a lesion detected by an AI algorithm. The window and level settings can be set automatically such that the mass, once detected by the AI algorithm, is optimally visualized. Processing block 2000 illustrates the step of performing an AI algorithm to detect a lesion (e.g., tumor). The preferred embodiment comprises neural networks, such as is described in U.S. patent application Ser. No. 16/506,073. Processing block 2001 illustrates the step of performing segmentation of the lesion. This can be accomplished by techniques described in U.S. Pat. No. 10,586,400. Processing block 2002 illustrates the step of performing segmentation of at least one surrounding structure (e.g., the organ from which the tumor arises). This can also be accomplished by techniques described in U.S. Pat. No. 10,586,400. Processing block 2003 illustrates the step of analyzing data units (e.g., Hounsfield Units) of the lesion (e.g., mean, standard deviation, range, etc.). Processing block 2004 illustrates the step of analyzing data units (e.g., Hounsfield Units) of the at least one surrounding structure (e.g., mean, standard deviation, range, etc.). Processing block 2005 illustrates the step of selecting visual representation adjustment logic for optimal visual analysis, which is further discussed in FIG. 21. Processing block 2006 illustrates the step of performing a single window/level option. Processing block 2007 illustrates the step of utilizing at least two different visual representation adjustment logic.

Figure 21:
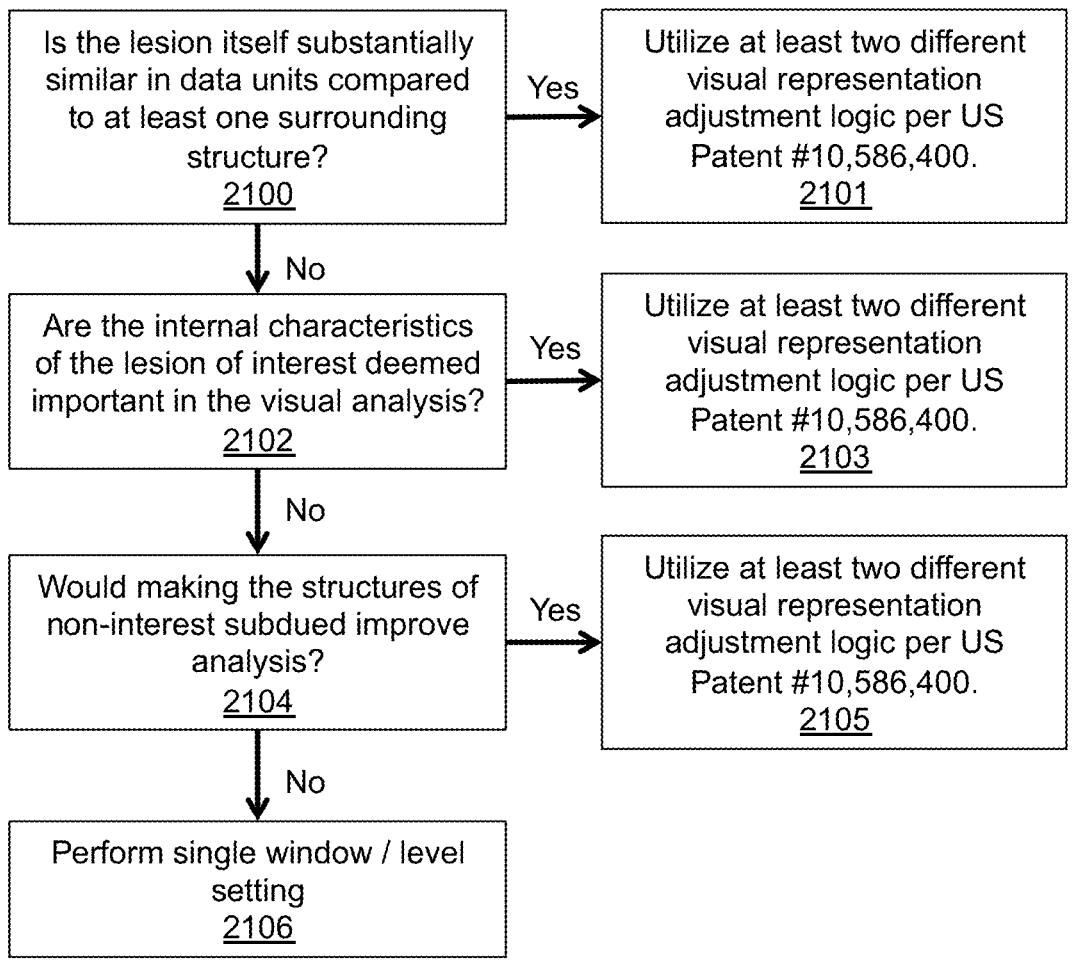
FIG. 21 illustrates a method of automatically performing window and level settings for improved viewing of a lesion detected by an AI algorithm.

FIG. 21 illustrates a method of automatically performing window and level settings for improved viewing of a lesion detected by an AI algorithm. As illustrated in FIG. 20, a single window/level setting could be performed or at least two different visual representation adjustment logic could be performed. This flow diagram illustrates an algorithm for determining which type of visual representation adjustment logic to perform. The decision tree is as follows.

In processing block 2100, the question of "is the lesion itself substantially similar in data units compared to at least one surrounding structure?" is raised. If the answer is yes, the proceed to processing block 2101. Processing block 2101 is to utilize at least two different visual representation adjustment logic per U.S. Pat. No. 10,586,400. Assume the lesion is a pancreatic cancer with a Hounsfield unit of 30 with a standard deviation of 5 Hounsfield Units and the pancreas has a has an average Hounsfield Unit of 32 with a standard deviation of 5 Hounsfield Units. There would be large overlap of the standard deviation error bars. This would be very poorly visualized using a single window and level setting wherein the pancreatic tumor is nearly indistinguishable from the pancreas itself. The dual windowing technique as described in U.S. Pat. No. 10,586,400 overcomes this limitation by performing segmentation and a dual windowing technique. If the answer to processing block 2100 is no, then proceed to processing block 2102. For example, a situation wherein the answer is no is a lesion that can easily be distinguished from the background. For example, assume a lesion in the liver has Hounsfield Units of 80 with a standard deviation of 5 and the background liver has Hounsfield Units of 30 with a standard deviation of 5. This is not substantially similar to the surrounding liver. Therefore, the next step is to proceed to processing block 2102.

In processing block 2102, the question "are the internal characteristics of the lesion of interest deemed important in the visual analysis?" is raised. If the answer is yes, then proceed to processing block 2103. Processing block 2103 is to utilize at least two different visual representation adjustment logic per U.S. Pat. No. 10,586,400. Assume that the lesion can easily be distinguished from the background. For example, assume a lesion in the liver has Hounsfield Units of 80 with a standard deviation of 5 and the background liver has Hounsfield Units of 30 with a standard deviation of 5. In order to best interpret the internal characteristics of the lesion and the surrounding liver tissue simultaneously, a dual window level setting can be applied. First, perform segmentation of the lesion and apply a window level setting of 80 to match the average Hounsfield Unit of the lesion and the window width of 50 so that the internal portions of the lesion demonstrate a variety of gray scale shades. Second, apply a window level setting of 30 and a window width to 50 to the remainder of the portions of the liver. This will allow superior visualization of the internal components of the liver lesion and the remainder of the liver lesion simultaneously. Note that other techniques in U.S. Pat. No. 10,586,400 can also be implemented. If the answer is no, then proceed to processing block 2104. For example, a situation wherein the answer to processing block 2102 is "no" is for example, a medical device implant, such as a saline breast implant. The radiologist may determine that there is little value in detailed examination of the inner aspect of a saline implant and may elect to forgo the dual windowing technique as described in U.S. Pat. No. 10,586,400.

In processing block 2104, the question of "would making the structures of non-interest subdued improve analysis?" is raised. If the answer is yes, then proceed to processing block 2105. Processing block 2105 is to utilize at least two different visual representation adjustment logic per U.S. Pat. No. 10,586,400. For example, if the radiologist is viewing a CT scan of the abdomen and the patient has taken oral contrast, then there will be a lot of high density material in the stomach and bowel loops. This may interfere with the ability to see the pancreas. Therefore, the radiologist may benefit from implementation of U.S. patent application Ser. No. 16/785,606, Improving image processing via a modified segmented structure. This patent provides a method of generating a modified segmented region around a structure and then allows at least two different visual representation adjustment logic per U.S. Pat. No. 10,586,400. This would be able to darken the areas around the pancreas and improve visualization of the pancreas. If the answer is no, proceed to processing block 2106. Processing block 2016 is to perform single window/level setting.

FIG. 22 illustrates the new scrolling technique implemented in this patent. For example, a constant image refresh rate of 0.16 seconds per slice is established. All slices wherein there is no event trigger are shown for 0.16 seconds. Note that slices that are determined to have a triggering event are given an alternative display in accordance with the matched predetermined response of a timer-dependent image refresh rate. For example, slices 1-3 were not noted to have a triggering event, thus a matched predetermined response of a timer-dependent image refresh rate is not applicable and the time spent under the of a timer-dependent image refresh rate is 0.16 seconds per slice. For example, slice 4 was noted to have a triggering event of the prior exam showing an abnormality at this location and the matched predetermined response of a timer-dependent image refresh rate is a 2.0 second delay. Note that there is an option to have an alert illustrating the triggering event with an image markup (e.g., red circle) at the site of the current scan where the abnormality was noted on the prior scan. For example, slices 5-6 were not noted to have a triggering event, thus a matched predetermined response of a timer-dependent image refresh rate is not applicable and the time spent under the new scrolling process is 0.16 seconds per slice. For example, slice 7 was noted to have a triggering event of the artificial intelligence (AI) algorithm detecting an abnormality at this slice and the matched predetermined response of a timer-dependent image refresh rate is a 3.5 second delay. Note that there is an option to have an alert illustrating the triggering event with a markup (e.g., red circle) at the site of the AI abnormality. Note that the markup can be shown for the whole 3.5 second delay or part of the 3.5 second delay (e.g., shown for the last 1.5 seconds). Also, note that the user can, of course, pause the scrolling for longer than 3.5 seconds if necessary. For example, slices 8-10 were not noted to have a triggering event, thus a matched predetermined response of a timer-dependent image refresh rate is not applicable and the time spent under the new timer-dependent image refresh rate is 0.16 seconds per slice. For example, slice 11 was noted to have a triggering event of the slice containing anatomy relevant to clinical history (e.g., right eye pain and slices contain right orbit) and the matched predetermined response of a timer-dependent image refresh rate is a 1.0 second delay per slice. Also, note that the user can, of course, pause the scrolling for longer than 3.5 seconds if necessary. For example, slices 12-13 were not noted to have a triggering event, thus a matched predetermined response of a timer-dependent image refresh rate is not applicable and the time spent under the new timer-dependent image refresh rate process is 0.16 seconds per slice. For example, slice 14 was noted to have a triggering event of the slice containing an anatomic feature that statistically needs more careful review (e.g., certain anatomic features, such as the pituitary stalk need more careful review than other anatomic features) and the matched predetermined response of a timer-dependent image refresh rate is a 1.5 second delay per slice. Also, note that the user can, of course, pause the scrolling for longer than 1.5 seconds if necessary. Note that the preferred embodiment is to assign a minimum time and fixation points to each anatomic structure in the body. For example, this system would be integrated with an eye tracking system for the radiologist. For example, for the sagittal midline slice through the brain, a certain amount of time (e.g., 1.5 seconds) and certain number of fixation points (e.g., 10) are needed within a certain distance (e.g., 1.0 cm) of the pituitary gland. A certain amount of time (e.g., 2.0 seconds) and certain number of fixation points (e.g., 15) are needed within a certain distance (e.g., 0.5 cm) of the pituitary stalk. A certain amount of time (e.g., 2.0 seconds) and certain number of fixation points (e.g., 20) are needed within a certain distance (e.g., 2.0 cm) of the midbrain. And so on. Another example organ where it is prudent for a radiologist to slow down is the pancreas, since pancreatic cancers are commonly missed since there are of similar Hounsfield Units to background pancreatic parenchyma. Furthermore, it would be possible to track radiologist alertness levels (e.g., via EEG analysis, via facial recognition) to assure that the radiologist performs the minimum number of fixation points and time while alert. This would serve to minimize error. For example, slices 15-18 were not noted to have a triggering event, thus a matched predetermined response of a timer-dependent image refresh rate is not applicable and the time spent under the new scrolling process is 0.16 seconds per slice. For example, slices 19-20 were noted to have a triggering event of the slice not containing patient data (e.g., imaged air gap above the patient's head), and the matched predetermined response of a timer-dependent image refresh rate is to have a 0.00 second delay and the time spent under the new scrolling process is 0.00 seconds per slice. This serves to speed up review of regions that do not contain patient data.

FIG. 23A illustrates an the integration of multiple factors to determine the optimum amount of time spent on each slice. An example algorithm to determine the optimum amount of time spent on each slice is as follows. Set a default time of 0.10 seconds per slice. Modify the default time by application of additional factors to determine the optimum amount of time to spend on each slice.

First, set a complexity scale ranging between 0 and 2. A value of "0" indicates a perfectly homogeneous image with standard deviation of 0 and would automatically cause the amount of time spent on that slice to be 0.01 seconds. A value of "1" indicates a mildly heterogeneous image (e.g., single anatomic feature with small standard deviation of less than 5 Hounsfield Units) and would indicate a 1× multiplier amount of time spent on that slice. A value of "2" indicates a moderately or severely heterogeneous image (e.g., more than one anatomic feature or standard deviation of more than 5 Hounsfield Units) and would indicate a 2× multiplier amount of time spent on that slice.

Second, set a size scale ranging between 0 and 2. A value of "0" indicated that there are no pixels containing anatomy on the image slices and would automatically cause the amount of time spent on that slice to be 0.01 seconds. A value of "1" indicates that there is less than 10 cm² of data on the slice and would indicate a 1× multiplier amount of time spent on that slice. A value of "2" indicates that there is greater than or equal to 10 cm² of data on the slice and would indicate a 2× multiplier amount of time spent on that slice.

Third, set a presence of pathology on prior examination additive factor. For example, a +2 second addition could be utilized if the same slice showed pathology on a prior examination. A +0 second addition could be utilized if the same slice showed no pathology on a prior examination. Note that the smart localization system as described in U.S. provisional patent application No. 62/939,685 can be utilized for improved localization from the current to prior examinations.

Fourth, set a finding detected by AI additive factor. For example, a +2 second addition could be utilized if the AI algorithm detected pathology. A +0 second addition could be utilized if the AI algorithm did not detect pathology. The preferred AI algorithm is a neural network. Other types of machine learning (ML) and computer aided detection (CAD) can also be incorporated.

The first row of the table shows the triggering events used in determining the timer-dependent image refresh rate. The second row shows slice number of 300, complexity of 0, size of image of 0, presence of pathology on prior examination as not applicable, the finding detected by AI of not applicable and time spent on the image slice 300 of 0.01 seconds. The third row shows slice number of 270, complexity of 1, size of image of 1, presence of pathology on prior examination as not applicable, the finding detected by AI of not applicable and time spent on the image slice 270 of 0.2 seconds. The fourth row shows slice number of 150, complexity of 2, size of image of 2, presence of pathology on prior examination as not applicable, and a positive finding detected by AI and time spent on the image slice 150 of 2.4 seconds. Note that this algorithm is equivalent to a regression. Note that it is also possible to integrate AI to determine the optimum amount of time to spend per slice. Additionally, eye tracking is an important factor at determining the amount of time spent on each slice and is discussed in detail in other sections of this patent. Note that a combination of embodiments can be performed. For example, use of a symbol combined with a pause. Combinations such as this would be invoked at the discretion of the radiologist. Clearly, other symbols could be used. A combination of pausing and identifying the region of concern by a symbol may be the best way to enhance accuracy of the radiologists while still retaining high productivity.

FIG. 23B illustrates application of the algorithm to a first example slice #300, which corresponds to the second row of the table in FIG. 23A. FIG. 23B is a slice that is in front of the patient's breast and contains no patient data, just the air in front of the breast. Using this algorithm, a radiologist saves 0.19 seconds on this slice. Cumulatively, over multiple slices, it saves several seconds. The second row shows slice number of 300, complexity of 0 (because there is no patient anatomic information), size of image of 0 (because there is no patient anatomic information), no prior pathology on prior examination at this location, the finding detected by AI of not applicable (because there is no patient anatomic data on the current examination) and time spent on the image slice 300 of 0.01 seconds.

FIG. 23C illustrates application of the algorithm to a first example slice #270, which corresponds to the third row of the table in FIG. 23A. FIG. 23C is a slice that is at the anterior most aspect of the breast and contains only a small amount of relatively homogeneous breast tissue. The third row shows slice number of 270, complexity of 1 (the breast tissue within the slice appears relatively homogeneous and is expected to have a small standard deviation), size of image of 1 (small size of less than 10 cm²), no prior pathology on prior examination at this location, no abnormality detected by AI at this location and time spent on the image slice 270 of 0.2 seconds.

FIG. 23D illustrates application of the algorithm to a first example slice #150, which corresponds to the fourth row of the table in FIG. 23A. This image contains a small enhancing breast cancer 2300. The fourth row shows slice number of 150, complexity of 2 (hetereogeneity of the breast), size of image of 2 (greater than 10 cm$^2$), no prior pathology on prior examination, and a positive finding detected by AI and time spent on the image slice 150 of 2.4 seconds.

Figure 24A:
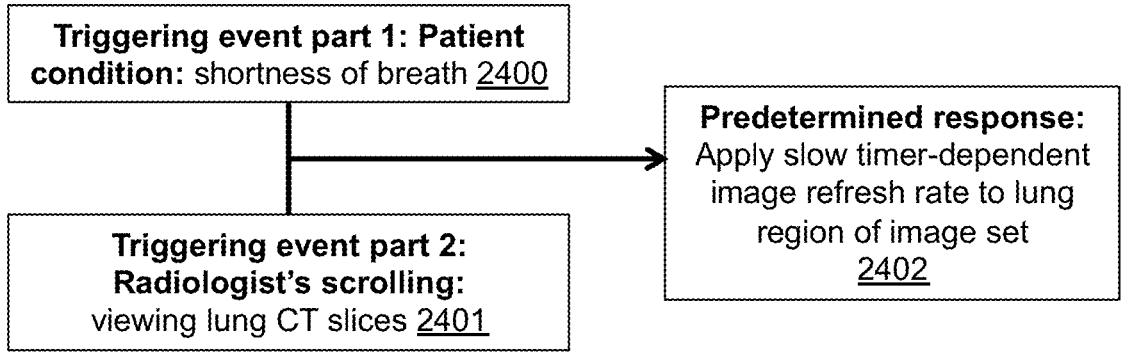
FIG. 24A illustrates a first example of patient's conditions wherein the embodiments could be employed to enhance radiologist's accuracy of diagnosis.

FIG. 24A illustrates a first example of patient's conditions wherein the embodiments could be employed to enhance radiologist's accuracy of diagnosis. The triggering event comprises when two parts occur at the same time. The first part of the triggering event is a symptom, such as shortness of breath 2400. The second part of the triggering event is when a certain portion of the examination, such as the CT slices including portions of the lungs 2401 is displayed. When these two events occur simultaneously, the triggering event has been established. The predetermined response of the timer-dependent image refresh rate is linked to the triggering event and occurs when the triggering event occurs. In this example, the predetermined response is a slow timer-dependent image refresh rate through the CT slices including portions of the lungs 2402. The patient's symptom of shortness of breath 2400 is correlated to the region being examined by a radiologist (e.g., lung) 2401. The rationale in this example is that the radiologist must pay special attention to the lung region and, therefore, if he/she probably should spend additional time (e.g., the embodiment of automatic pausing for a specified period on each slice during scrolling) on each slice that contains lung tissue. By using this pausing during the scroll, the probability of correct diagnosis would be enhanced. The radiologist could turn the smart scrolling function on and off, as needed to enhance overall speed and accuracy of the review.

Figure 24B:
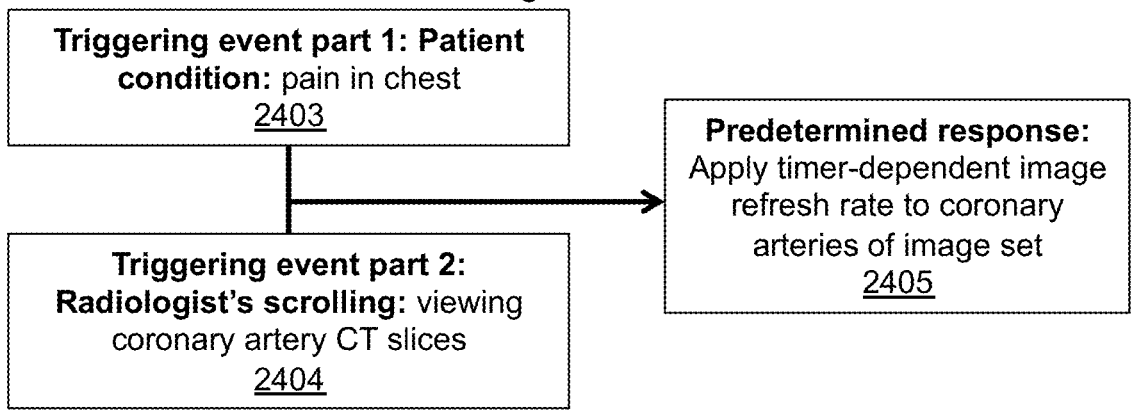
FIG. 24B illustrates a second example of patient's conditions wherein the embodiments could be employed to enhance radiologist's accuracy of diagnosis.

FIG. 24B illustrates a second example of patient's conditions wherein the embodiments could be employed to enhance radiologist's accuracy of diagnosis. The triggering event comprises when two parts occur at the same time. The first part of the triggering event is a symptom, such as pain in the chest 2403. The second part of the triggering event is when a radiologist scrolls to a certain portion of the examination, such as the CT slices including portions of the coronary arteries 2404. When these two events occur simultaneously, the triggering event has been established. The predetermined response is linked to the triggering event and occurs when the triggering event occurs. In this example, the predetermined response is slow timer-dependent image refresh rate through the CT slices including portions of the coronary arteries 2405 wherein the patient's symptom of chest pain 2403 is correlated to the region being examined by a radiologist (e.g., coronary arteries) 2404. The rationale in this example is that the radiologist must pay special attention to the coronary arteries and, therefore, if he/she probably should spend additional time (e.g., the embodiment of automatic pausing for a specified period on each slice during scrolling) on each slice that contains coronary arteries. By using this pausing during the scroll, the probability of correct diagnosis would be enhanced. The radiologist could turn the smart scrolling function on and off, as needed to enhance overall speed and accuracy of the review. A differential diagnosis is required and special attention to potential areas is required. Note that since there are multiple possible causes of chest pain, the preferred embodiment is to have multiple combinations of triggering events matched to multiple predetermined responses. If the patient presented with pain in the chest, the medical image slices containing portions of the heart could be treated as explained contained in the Summary section. The logic in this example is that the patient may have suffered a heart attack and the slices containing heart tissue needed careful examination. Alternatively, initial examining physician reported that the patient had been is an automobile accident, then the area of focus would be the bone structure.

Figure 24C:
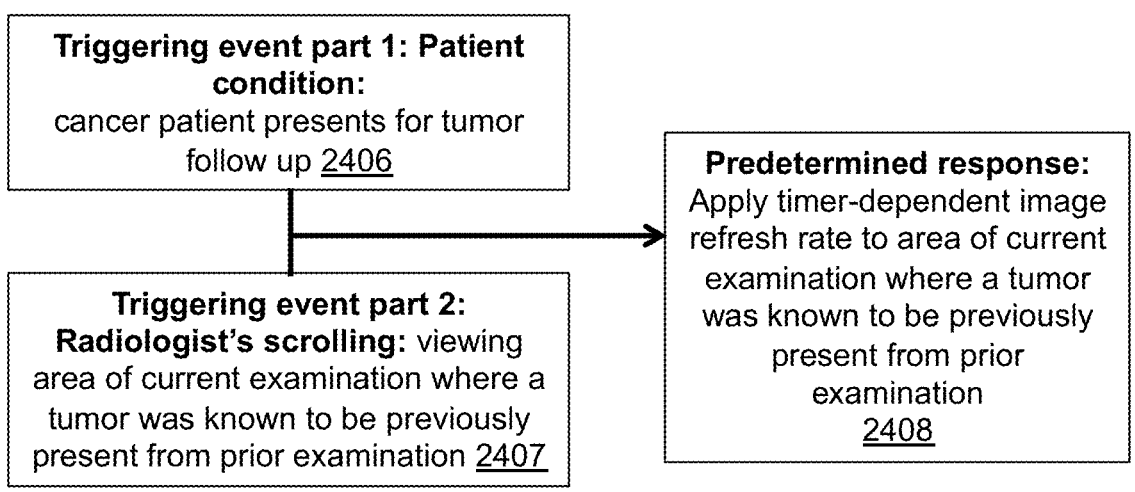
FIG. 24C illustrates a third example of patient's conditions wherein the embodiments could be employed to enhance radiologist's accuracy of diagnosis.

FIG. 24C illustrates a third example of patient's conditions wherein the embodiments could be employed to enhance radiologist's accuracy of diagnosis. The triggering event comprises when two parts occur at the same time. The first part of the triggering event is the purpose of the examination, such as a cancer patient presenting for tumor follow up 2406. The second part of the triggering event is when a radiologist scrolls to a certain portion of the examination, such as the area of the current examination where a tumor was known to be previously present from the prior examination 2407. When these two events occur simultaneously, the triggering event has been established. The predetermined response of the slow timer-dependent image refresh rate is linked to the triggering event and occurs when the triggering event occurs. In this example, the predetermined response is the slow timer-dependent image refresh rate through the area of the current examination where a tumor was known to be previously present from a prior imaging examination 2408 wherein the cancer patient presenting for tumor follow up 2406 is correlated to the region being examined by a radiologist (e.g., the area of the current examination where a tumor was known to be previously present from a prior imaging examination) 2407. The rationale in this example is that the radiologist must pay special attention to the area of the current examination where a tumor was known to be previously present from a prior imaging examination and, therefore, if he/she probably should spend additional time (e.g., the embodiment of automatic pausing for a specified period on each slice implemented by the timer-dependent image refresh rate) on each slice that contains area of the current examination where a tumor was known to be previously present from a prior imaging examination. By using this pausing during the scroll, the probability of correct diagnosis would be enhanced. The radiologist could turn the smart scrolling function on and off, as needed to enhance overall speed and accuracy of the review. If the patient in for a scheduled appointment for follow up on status of a tumor, the medical images from a previous imaging session could be retrieved and displayed in conjunction with currently obtained medical images. The scrolling process embodiment of pausing could be applied to both current and previous images simultaneously to look back and forth and make a careful assessment of changes, if any, in the tumor.

FIG. 25A illustrates a slice of (e.g., slice N within the sequence) a set of medical images which is displayed for a duration of 0.25 seconds (note: this particular slice is not linked to a triggering event to cause a predetermined response of a slowing or speeding of the timer-dependent image refresh rate). This is an example of the short time duration (e.g., 0.25 seconds) that a radiologist, using the two finger on mouse roller ball technique, would typically spend examining an individual slice of medical imagery. During this time, he/she is expected to discern anomalous tissue which may be small in physical size and have a gray scale very close to that of adjacent tissue. Every person's body is different and this not a case of looking at a standard structural layout and trying to pick out a small change. It is a very real challenge to get an accurate diagnosis and make this diagnosis within tight time constraints. This particular figure is an arbitrary slice within a set of medical images and, for discussion purposes, the first in a sequence. For illustration purposes, there is no triggering event (e.g., relevant patient data, AI detected abnormality, etc.) pertaining to this particular slice.

FIG. 25B illustrates a slice of (e.g., slice N+1 within the sequence) a set of medical images which is displayed for a duration of 0.25 seconds (note: this particular slice is not linked to a triggering event to cause a predetermined response of a slowing or speeding of the timer-dependent image refresh rate). This is the next slice in the set of medical images—the second slice in the illustration sequence. For illustration purposes, there is also no triggering event (e.g., relevant patient data, AI detected abnormality, etc.) pertaining to this particular slice, hence the radiologist again spends only 0.25 seconds on this slice.

FIG. 25C illustrates a slice of (e.g., slice N+2 within the sequence) a set of medical images which is displayed for a duration of 3.5 seconds (note: this particular slice is linked to a region(s) pertaining to a triggering event and the predetermined response is to cause the slice to be displayed for 3.5 seconds). Army studies have investigated how long it takes to find a target is differing types of areas. The average results vary from 3-5 seconds depending on the complexity of the scene. As the scene becomes more complex, it becomes impossible for some individuals to locate the target. It is reasonable that, if the anomalous tissue is small and the gray scale blends in with the surrounding tissue in the slice, it will take a radiologist about the same time to locate this anomalous tissue. So, for the purpose of illustrating a pause in this figure, an automatic pause is injected into the scrolling process (e.g., due to a triggering event of an AI identified finding) to permit the radiologist to better study the display at hand and, if anomalous tissue is present, have a significantly improved chance of finding this tissue and making a more accurate diagnosis. Note that on this N+2 slice in the sequence a time of 3.5 seconds was injected into the timing during which of the medical image displayed is paused. This pause was automatically injected into the scrolling when there was a triggering event pertaining to this particular slice. This 3.5 seconds is for illustrative purposes only and the pause duration would be established by other means. In this example, the triggering event was a small focus of intraventricular hemorrhage 2501 detected by an artificial intelligence algorithm.

FIG. 25D illustrates a slice of (e.g., slice N+3 within the sequence) a set of medical images which is displayed for a duration of 3.5 seconds (note: this particular slice is linked to a region(s) pertaining to a triggering event and the predetermined response is to cause the slice to be displayed for 3.5 seconds). There was a triggering event pertaining to this particular slice and, therefore, a 3.5 second pause was automatically injected into the scrolling process. In this example, the triggering event was a small focus of intraventricular hemorrhage 2502 detected by an artificial intelligence algorithm. Note: a fruitful area for study spawned by this patent would be to investigate false negative rates as a function of scroll rates. It is anticipated that a variety of publications will emerge. These studies could be the basis for setting nominal values.

FIG. 25E illustrates a slice of (e.g., slice N+4 within the sequence) a set of medical images which is displayed for a duration of 0.25 seconds (note: this particular slice is not linked to a triggering event to cause a predetermined response of a slowing or speeding of the timer-dependent image refresh rate). This $5^{th}$ slice in the sequence has no triggering event pertaining to this particular slice, hence the radiologist again spends only 0.25 seconds on this slice.

FIG. 25F illustrates a slice of (e.g., slice N+5 within the sequence) a set of medical images which is displayed for a duration of 0.25 seconds (note: this particular slice is not linked to a triggering event to cause a predetermined response of a slowing or speeding of the timer-dependent image refresh rate). This $5^{th}$ slice in the sequence has no triggering event pertaining to this particular slice, hence the radiologist again spends only 0.25 seconds on this slice.

Figure 26A:
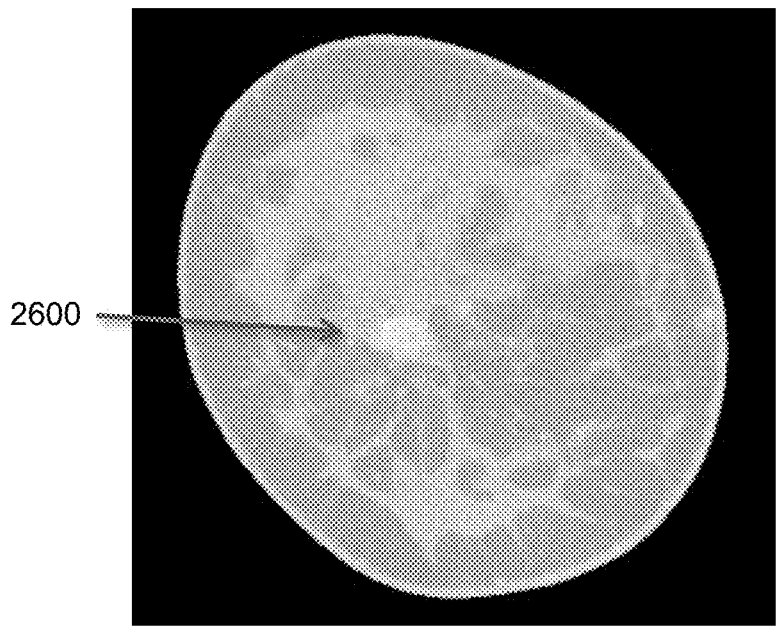
FIG. 26A illustrates a slice of medical imagery which has, within the slice, a tumor at time point #2.

FIG. 26A illustrates a slice of medical imagery which has, within the slice, a tumor at time point #2. The imagery was recently taken (e.g., in 2020). The tumor 2600 in the year 2020 is shown. One of the key tasks for a radiologist is to track changes, if any, in tumors over time. Patients accumulate sets of medical images taken over months/tears. The question arises whether any change has occurred that may indicate a change of patient's condition. Hence the question whether the tumor has changed in either size or shape for this current image (e.g., in 2020) slice as compared to one taken previously month(s)/year(s) ago.

Figure 26B:
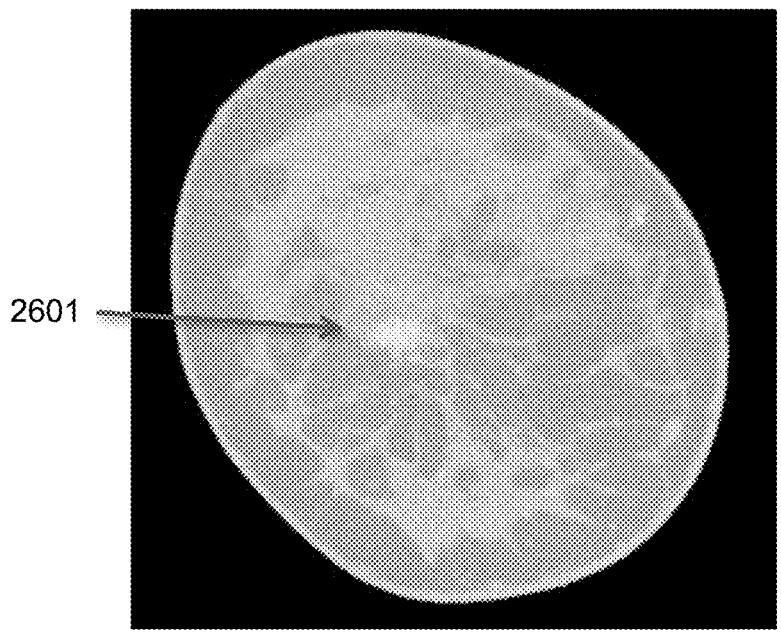
FIG. 26B illustrates a slice of medical imagery which has, within the slice, a tumor at time point #1.

FIG. 26B illustrates a slice of medical imagery which has, within the slice, a tumor at time point #1. This slice of medical imagery was previously taken (e.g., in 2019) and retrieved from patient's records and displayed for comparative purposes. The tumor 1301 is shown at 2019. Under this patent, the previous image set would be retrieved from the patient's records and displayed simultaneously with the current images. Note that the smart localization system as described in U.S. provisional patent application No. 62/939,685 can be utilized for improved localization from 2019 to 2020 examinations. The portions of the both image sets containing the tumor would be displayed side-by-side. The scrolling can be rapid through non-tumor containing slices, but a mandatory slow down can be implemented during the tumor containing slices (e.g., an AI algorithm detects a tumor and this serves as a triggering event, which causes a predetermined response of a timer-dependent image refresh rate. The scrolling process embodiment of pausing could be applied to both current and previous images simultaneously to look back and forth make a careful assessment of changes, if any, in the tumor. Subjectively, the size of the tumor appears to have grown when comparing the tumor 2600 in the year 2020 with the tumor 2601 in the year 2019.

Figure 27:
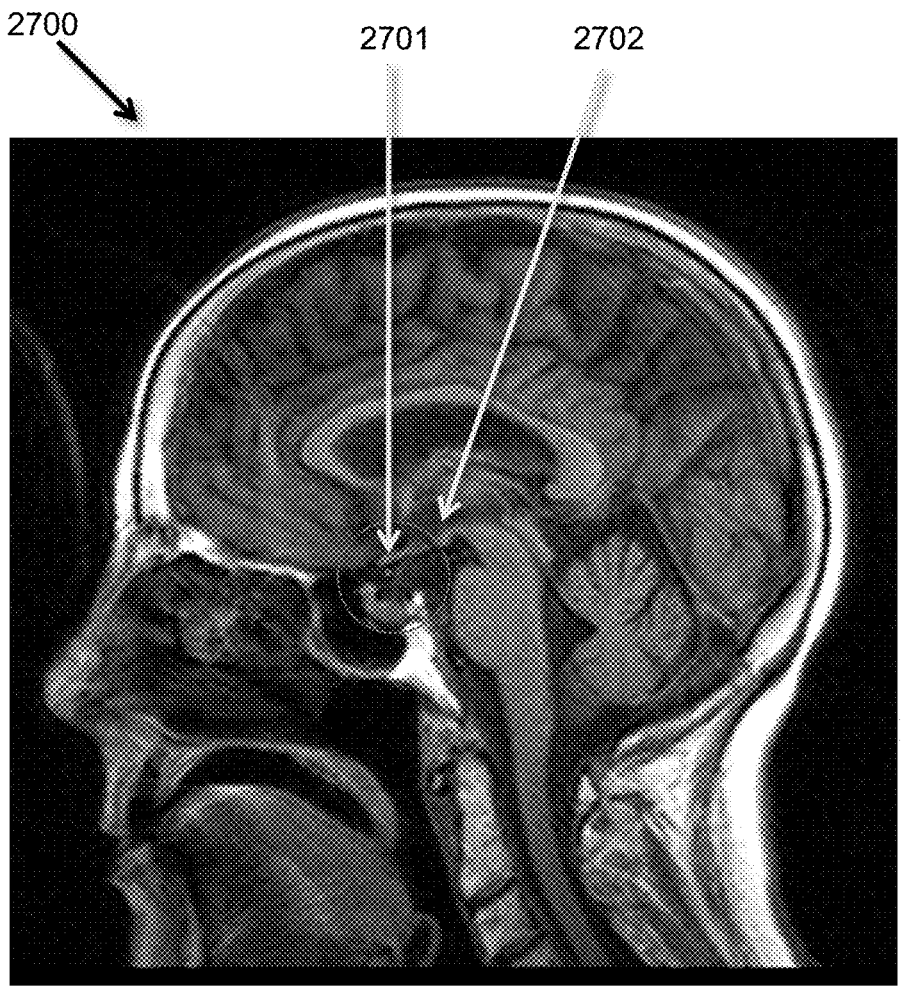
FIG. 27 illustrates an example type of triggering event including utilization of eye tracking in relation to anatomic feature.

FIG. 27 illustrates an example type of triggering event including utilization of eye tracking in relation to anatomic feature. An example algorithm to accomplish this is discussed. A midline sagittal Mill image of the brain is shown 2700. First, an eye tracking system is established, as is described in U.S. Provisional Patent Application 62/985,363. Next, the pituitary stalk is segmented (e.g., atlas based segmentation). The midpoint of the pituitary stalk is determined. Assume the slice is an in the (x, y) plane. This point can be determined by taking the highest x-direction pixel pertaining to the pituitary talk and the lowest x-direction pixel pertaining to the pituitary stalk and averaging these two x-values to determine the midpoint of the pituitary stalk in the x-direction called "mid-x-point-of-pituitary-stalk". Next, take the highest y-direction pixel pertaining to the pituitary talk and the lowest y-direction pixel pertaining to the pituitary stalk and averaging these two y-values to determine the midpoint of the pituitary stalk in the y-direction, called "mid-y-point-of-pituitary-stalk". Thus, the center point 2701 (shown as a red dot for illustrative purposes only) of the pituitary stalk can be determined, by this algorithm, to be the pixel located at ("mid-x-point-of-pituitary-stalk", "mid-y-point-of-pituitary-stalk"). Next, take all pixels within a 1.5 cm radius of this value (shown as a red circle 2702 for illustrative purposes only). Note that an example triggering event would be the achievement of 1.5 seconds looking in this region and a minimum of 5 fixation points. This would indicate that the structure has adequately been inspected by the radiologist. An example predetermined response would be to lock the image via the timer-dependent image refresh rate until the requisite triggering event (time and number of fixation points) has been performed on each anatomic structure or at least the critical anatomic structures. In the event that the radiologist has not achieved the requisite triggering event (time and number of fixation points), an alert method (e.g., annotation such as a red circle 2702) can be utilized to increase the number of fixation spots at that anatomic feature.

Figure 28A:
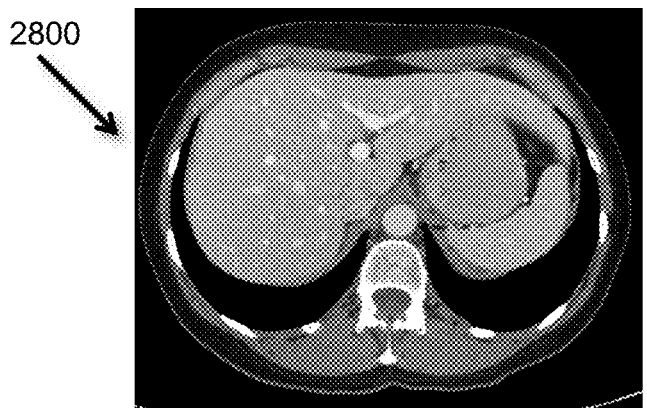
FIG. 28A illustrates a slice with conventional "abdomen window and level" setting.

FIG. 28A illustrates a slice with conventional "abdomen window and level" setting. 2800 shows a CT slice with a window level setting of 40 and window width setting of 350.

Figure 28B:
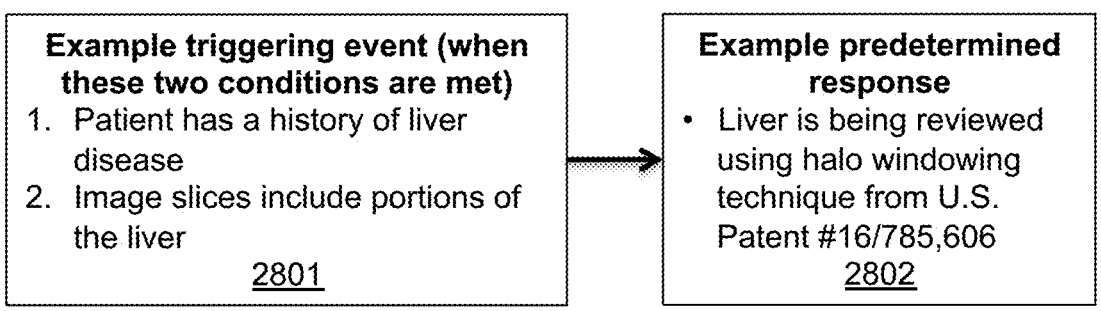
FIG. 28B illustrates a text box with an example 3-pronged triggering event and a matched predetermined response of an image-dependent viewing parameter.

FIG. 28B illustrates the text box with a two-pronged triggering event and a matched predetermined response of an image-dependent viewing parameter.

When the following two conditions are met, the triggering event is established. A text box 2801 is shown. First, the person has must have a history of liver disease. Second, the image slices must include portions of the liver. A text box 2802 is shown. This is an example of a predetermined response. The liver is being reviewed using halo windowing technique, as described in U.S. patent application Ser. No. 16/785,606.

Figure 28C:
FIG. 28C illustrates a second example of "halo windowing" as described in U.S. patent application Ser. No. 16/785,606.

FIG. 28C illustrates a second example of "halo windowing" as described in U.S. patent application Ser. No. 16/785,606. 2803 illustrates the CT slice with "halo windowing. 2804 illustrates the liver with optimized grayscale setting for the liver is set with a window level of 117 and a window width of 166, which is the best possible settings for visualization of the liver. 2805 illustrates a modified segmented region with a "halo" appearance with a window level grayscale setting for the liver halo set with a window level of 71 and window width of 357. 2806 illustrates window level grayscale setting for the remainder of the structures in the CT slice is set with a window level of 475 and window width of 2618. This overall process improves upon the existing art by modifying the images so that the user (e.g., radiologist) focuses on the liver during the liver portion of the examination and is not distracted by other bright voxels. In some embodiments, multiple halos with each halo having a unique window level setting can be performed so as to slowly alter the window level settings in a radial fashion outward from the organ. Thus, the triggering event causes the slice to have increased contrast of a region(s) pertaining to the patient medical condition (e.g., liver disease). One of the embodiments of this patent to alert the radiologist that there is relevant patient data pertaining to this particular slice is to change the contrast of the region containing tissue of that region with respect to the surrounding tissue. During the fast scrolling process this change in contrast could alert the radiologist of the presence of relevant information. Other options include displaying all non-important findings (as determined by AI) as subdued and all important findings (as determined by AI) with optimized contrast. The radiologist would then have the option of self-initiated slowing, automatic slowing or pausing the scrolling process. In this figure the liver has increased contrast. In addition, this slice also has decreased contrast external to a region(s) pertaining to the patient medical condition data. Specifically, it decreases the contrast of tissue not relevant to patient data (e.g., liver disease) pertaining to this particular slice. If volume rendering were performed, an option would be to change the transparency and thus achieve the same alerting function. It should be noted that these changes in contrast/transparency could be automatically combined with a pause function. Multiple combinations could occur in accordance with method disclosed in U.S. patent Ser. No. 16/785,606.

FIG. 29A illustrates applications of image-dependent viewing parameters for advanced viewing on extended reality displays. Advanced technologies are being introduced to the radiological community. A text box 2900 is shown. For example, by creating a 3D volume out of the 2D medical slices and presenting a slightly different picture to each eye in a head display unit such that the radiologist see a 3D version of the patient's anatomy. Examples of image-dependent viewing parameters for advanced viewing on Extended Reality displays include: rotating the imaging volume; changing the location of the viewing perspective; zooming; and, converging.

FIG. 29B illustrates a left eye view of a breast cancer within that has undergone the segmentation process with non-breast cancer matter subtracted through a filtration process. Note that a 3D volume cursor 2901 surrounds the breast cancer lesion. In this figure the breast cancer has been segmented out and is located inside the 3D volume cursor 2901.

FIG. 29C illustrates a right eye view of a breast cancer within that has undergone the segmentation process with non-breast cancer matter subtracted through a filtration process. Note that a 3D volume cursor 2901 surrounds the breast cancer lesion. In this figure the breast cancer has been segmented out and is located inside the 3D volume cursor 2901.

FIG. 29D illustrates a left eye view of a breast cancer within that has undergone the segmentation process with non-breast cancer matter subtracted through a filtration process with the viewing position zoomed inward closer to the breast cancer, as compared to the viewing position from FIG. 29B. Note that with the zoomed in position, the key anatomic features are enlarged on the screen. This enables a higher number of fixation points per unit area and may improve characterization of subtle imaging features. For example, the spiculated margins of the tumor, as denoted by the arrows 2902, circle 2903 can be appreciated on the zoomed in viewing, as seen in FIG. 29D, but not well appreciated in FIG. 29B. With this enlargement, however, the breast cancer becomes more noticeable thus improving probability of detection and accuracy of characterization by the radiologist, which is caused by an increased number of fixation points on the breast cancer during saccadian eye movements.

FIG. 29E illustrates a right eye view of a breast cancer within that has undergone the segmentation process with non-breast cancer matter subtracted through a filtration process with the viewing position zoomed inward closer to the breast cancer, as compared to the viewing position from FIG. 29C. Note that with the zoomed in position, the key anatomic features are enlarged on the screen. This enables a higher number of fixation points per unit area and may improve characterization of subtle imaging features. For example, the spiculated margins of the tumor, as denoted by the arrows 2902, circle 2903 can be appreciated on the zoomed in viewing, as seen in FIG. 29E, but not well appreciated in FIG. 29C. With this enlargement, however, the breast cancer becomes more noticeable thus improving probability of detection and and accuracy of characterization by the radiologist, which is caused by an increased number of fixation points on the breast cancer during saccadian eye movements.

Figure 30A:
FIG. 30A illustrates an annotation of a particular region of interest on a slice by an arrow pointing to a region(s) pertaining to a finding identified by a CAD/AI algorithm, which is an example of a notification of a triggering event.

FIG. 30A illustrates annotation of a particular region of interest on a slice by an arrow pointing to a region(s) pertaining to a finding identified by a CAD/AI algorithm, which is an example of a notification of a triggering event. 3000 illustrates a CT slice. This figure illustrates use of an external symbol to annotate an area or region relevant patient data pertaining to this particular slice. An arrow 3001 was the symbol selected for this annotation and is placed and oriented such that the radiologist can quickly spot the area of concern per the AI finding. (In this particular image, an automated measurement of percentage of stenosis on the left anterior descending artery is performed with an arrow 3001 placed at a site of stenosis aligned perpendicular to the direction of the artery.) Note that an option is for a red arrow 3001 to appear during a portion of the time period of the visualization of the slice rather than throughout the entirety of the time period when the slice is displayed. The advantage of this would be for the radiologist to be able to view the whole image on his own and not be distracted by the finding identified by a computer aided detection or AI algorithm for a period of time and then following this period be able to see the finding identified by a computer aided detection or AI algorithm. These markers serve to indicate that a triggering event has occurred on this particular slice. The radiologist, having this information, could self-initiate the process of pausing or a pause could be initiated through implementation of a timer-dependent image refresh rate.

Figure 30B:
FIG. 30B illustrates an annotation of a particular region of interest on a slice by a circle encircling a region(s) pertaining to a finding identified by a CAD/AI algorithm, which is an example of a notification of a triggering event.

FIG. 30B illustrates annotation of a particular region of interest on a slice by a circle encircling a region(s) pertaining to a finding identified by a CAD/AI algorithm, which is an example of a notification of a triggering event. 3000 illustrates a CT slice. This is the same image as FIG. 30A with a change of symbol from arrow 3001 to circle 3002 surrounding the area detected by CAD/AI. Note that there is a multitude of symbols which could be selected, two of which are depicted in this FIG. 30B and FIG. 30A. A variety of colors, shapes, dashes/solid/widths of lines could be used to draw attention to the region(s) relevant patient data pertaining to this particular slice. These markers serve to indicate that a triggering event has occurred on this particular slice. The radiologist, having this information, could self-initiate the process of pausing or a pause could be initiated through implementation of a timer-dependent image refresh rate.

Figure 30C:
FIG. 30C illustrates an annotation of the outer edges of the slice with a colored line pertaining to a finding identified by a CAD/AI algorithm, which is an example of a notification of a triggering event.

FIG. 30C illustrates annotation of the outer edges of the slice with a colored line pertaining to a finding identified by a CAD/AI algorithm, which is an example of a notification of a triggering event. 3000 illustrates a CT slice. The border of the slice 3003 is an example method to draw attention to the fact that a triggering event has occurred on this particular slice. The radiologist, having this information, could self-initiate the process of pausing or a pause could be initiated through implementation of a timer-dependent image refresh rate.

Figure 31A:
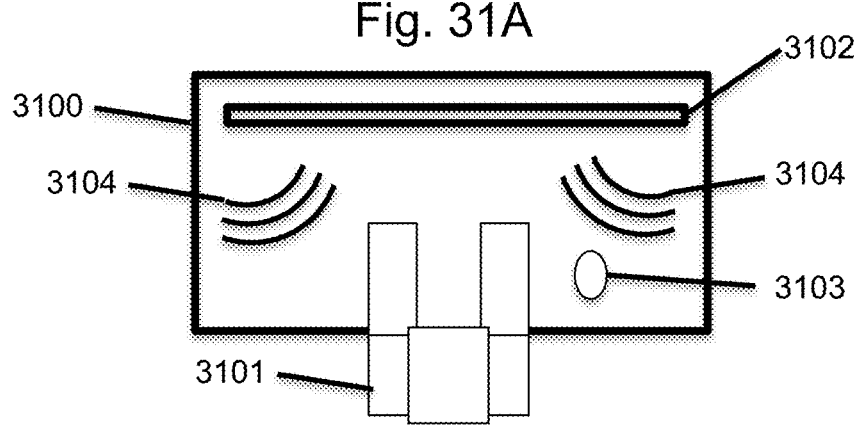
FIG. 31A illustrates an example layout of a radiologist workstation with an audio addition (transmit only or transmit/receive) to alert the radiologist the slice(s) displayed are to a region(s) indicating that a triggering event has occurred.

FIG. 31A illustrates an example layout of a radiologist workstation with an audio addition (transmit only or transmit/receive) to alert the radiologist the slice(s) displayed are to a region(s) indicating that a triggering event has occurred. 3100 illustrates the radiologist's desk. 3101 illustrates the radiologist. 3102 illustrates the radiology monitor. 3103 illustrates the radiologist's mouse. 3104 illustrates the audio signal emitted from speakers. This figure illustrates the use of an audio device integral with the radiologist workstation. The audio signal would be at least one of the following: a continuous signal during the time when a slice is displayed to draw attention to the fact this is region relevant patient data pertaining to this particular slice; signal the start and/or end of a set of slices with relevant data; be of a variety of tomes and volume, be selected by default or by the individual radiologist. The receive function of the audio device, if present, could be used in conjunction with the preparation of notes for the report or start/stop the pause function, or go to the relevant patient data. Note that some triggering events would be tied to the sound alert and other triggering events would not be tied to the sound alert. The radiologist, having this information, could self-initiate the process of pausing or a pause could be initiated through implementation of a timer-dependent image refresh rate.

Figure 31B:
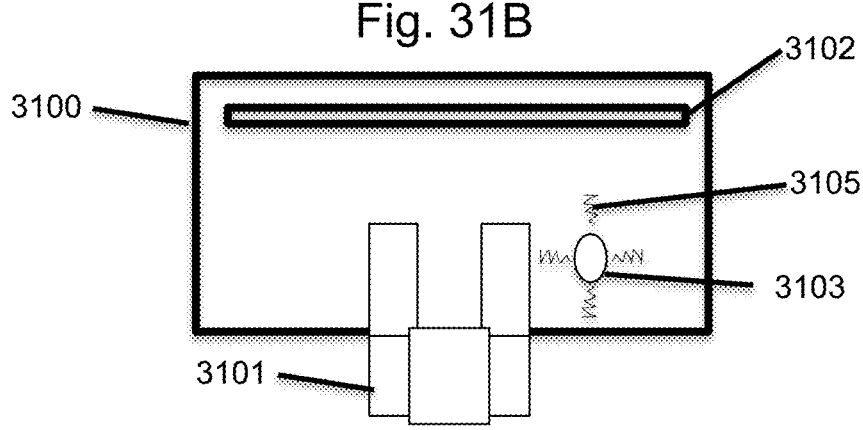
FIG. 31B illustrates an example layout of a radiologist workstation with a vibration mechanism to alert the radiologist the slice(s) displayed are to a region(s) indicating that a triggering event has occurred.

FIG. 31B illustrates an example layout of a radiologist workstation with a vibration mechanism to alert the radiologist the slice(s) displayed are to a region(s) indicating that a triggering event has occurred. 3100 illustrates the radiologist's desk. 3101 illustrates the radiologist. 3102 illustrates the radiology monitor. 3103 illustrates the radiologist's mouse. 3105 illustrates a buzzing vibration emitted from the radiologist's mouse. This vibration device 3105 would serve the same purpose as the audio transmit device but, instead provide tactile data. For example, a mouse with buzzer. Note that some triggering events would be tied to the vibration alert and other triggering events would not be tied to the vibration alert. The radiologist, having this information, could self-initiate the process of pausing or a pause could be initiated through implementation of a timer-dependent image refresh rate.

Figure 31C:
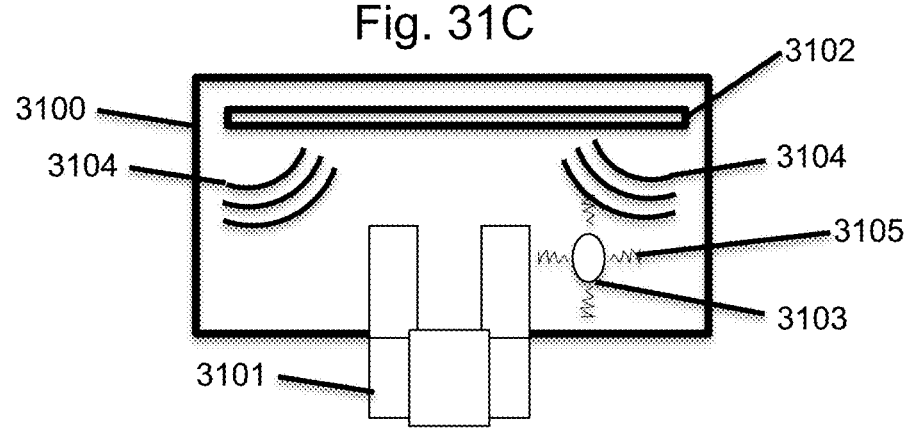
FIG. 31C illustrates an example layout of a radiologist workstation with a buzzer that both emits a sound and also vibrates to alert the radiologist the slice(s) displayed are to a region(s) indicating that a triggering event has occurred.

FIG. 31C illustrates an example layout of a radiologist workstation with a buzzer that both emits a sound and also vibrates to alert the radiologist the slice(s) displayed are to a region(s) indicating that a triggering event has occurred. 3100 illustrates the radiologist's desk. 3101 illustrates the radiologist. 3102 illustrates the radiology monitor. 3103 illustrates the radiologist's mouse. 3104 illustrates the audio signal emitted from speakers. 3105 illustrates a buzzing vibration emitted from the radiologist's mouse 3103. This device combines both audio 3104 and vibration 3105 capabilities. These attachments shown (or integral to the workstation through software) draw attention to the fact this is region contains a triggering event. The radiologist, having this information, could self-initiate the process of changing imaging refresh rate or pausing. Note that some triggering events can be tied to the sounds and vibration and other triggering events would not be tied to the sounds and vibration. The radiologist, having this information, could self-initiate the process of pausing or a pause could be initiated through implementation of a timer-dependent image refresh rate.

FIG. 32A illustrates a flow chart showing the triggering event criteria and the matched predetermined response of a timer-dependent image refresh rate. In this example, the triggering event criteria 3200 is that a fixation point must be within 4.0 cm of every liver pixel. Note that liver segmentation needs to be performed. The predetermined response 3201 is for the timer-dependent image refresh rate to move to the next slice. This overall process would allow a natural viewing of an image and scrolling pattern to roll through the images slice-by-slice once each image is comprehensively viewed.

FIG. 32B illustrates application of the triggering event criteria and the matched predetermined response in FIG. 32A. 3202 is a text box illustrating time=0.00 seconds, which is the instant at which this slice 3203 appeared. 3203 illustrates a CT slice of the liver with dual windowing technique, as described in U.S. Pat. No. 10,586,400. 3204 illustrates a processing block determining whether or not the triggering event has been met and in this case the triggering event has not been bet as there is not a fixation point (as determined by an eye tracking system) within 4.0 cm of every liver pixel. 3205 illustrates a processing block illustrating that no predetermined response of the timer-dependent image refresh rate is performed. The next step is therefore to assess for triggering event at the next time interval. 3206 is a text box illustrating time=0.25 seconds, which indicates that the radiologist has had 0.25 seconds to view this slice thus far. 3207 illustrates a CT slice of the liver with dual windowing technique, as described in U.S. Pat. No. 10,586,400 including 4 fixation points (shown as small yellow dots on the liver) that have occurred since time=0.00 seconds. 3208 illustrates a processing block determining whether or not the triggering event has been met and in this case the triggering event has not been bet as there is not a fixation point (as determined by an eye tracking system) within 4.0 cm of every liver pixel. 3209 illustrates a processing block illustrating that no predetermined response of the timer-dependent image refresh rate is performed. The next step is therefore to assess for triggering event at the next time interval. 3210 is a text box illustrating time=0.50 seconds, which indicates that the radiologist has had 0.50 seconds to view this slice thus far. 3211 illustrates a CT slice of the liver with dual windowing technique, as described in U.S. Pat. No. 10,586,400 including 8 fixation points (shown as small yellow dots on the liver) that have occurred since time=0.00 seconds. 3212 illustrates a processing block determining whether or not the triggering event has been met and in this case the triggering event has been bet as there is a fixation point (as determined by an eye tracking system) within 4.0 cm of every liver pixel. 3213 illustrates a processing block illustrating that the predetermined response of the timer-dependent image refresh rate is to be performed. The next step is therefore to perform the triggering event and reset the clock. 3214 is a text box illustrating time=0.00 seconds, which is the instant at which this slice 3215 appeared. 3215 illustrates a CT slice of the liver with dual windowing technique, as described in U.S. Pat. No. 10,586,400. Note that this is the instant at which the slice 3215 appeared, so there are no fixation points yet. 3216 illustrates a processing block determining whether or not the triggering event has been met and in this case the triggering event has not been bet as there is not a fixation point (as determined by an eye tracking system) within 4.0 cm of every liver pixel. 3217 illustrates a processing block illustrating that no predetermined response of the timer-dependent image refresh rate is performed. The next step is therefore to assess for triggering event at the next time interval and continue this process.

FIG. 33 illustrates the integration of triggering events, timer-dependent image refresh rate, image-dependent viewing parameter, and image-dependent reporting parameter utilization into the interpretation of a chest x-ray.

The first time interval during the image interpretation is the time period from when the image is first shown to 3.00 seconds. The displayed image is a window level setting of 3,000 and a window width of 30,000, which provides fairly good contrast for all anatomic structures in the field of view. The timer-dependent refresh rate utilized for this first time interval is comprised of two components. Both of the timer-dependent image refresh rates have to be satisfied in order to achieve wherein a new image can appear. The first component of the timer-dependent image refresh rate is a minimum delay for 3.00 seconds. The second component of the timer-dependent image refresh rate is a minimum of 4 fixation points including at least one in each quadrant of the image. In this example, the user performed 4 fixation points including at least one in each quadrant of the image by the time point of 2.00 seconds thereby satisfying the second timer-dependent image refresh rate component. However, the first component of the timer-dependent image refresh rate was not satisfied until 3.00 seconds. Therefore, after and only after an additional 1.00 seconds have passed will both the first and second components be satisfied. During that additional 1.00 seconds, the user has performed one additional fixation point for a total of 5. The location of the fixation points during this time interval is shown. Thus, in this example, the rate limiting event is the first component. The completion of the timer-dependent refresh rate criteria acts as a triggering event for both the first image-dependent viewing parameter and the first image-dependent reporting parameter, which are therefore both implemented at 3.00 seconds. The image dependent reporting parameter does not enter data during this step. At time mark 3.00 seconds, both aspects of the image-dependent viewing parameter at this moment are implemented. Zooming setting is selected in order to maximize detection of pathology occurring within the trachea. The image-dependent viewing parameter is zooming in an dual windowing. Please see U.S. Pat. No. 10,586,400 and U.S. patent application Ser. No. 16/785,506 for details on how to perform the dual-windowing technique. The dual windowing setting shown in this example has a window level of 3,000 and a window width of 30,000 for the trachea. For all other structures in the field of view, a window level setting of 50,000 and window width setting of 120,000 is implemented. Also, please note that a halo is utilized to gradually show transition between the two different window width and window level settings. At time mark 3.00 seconds, both aspects of the image-dependent reporting parameter are implemented. The first aspect is the automatic transition into the trachea section of the radiology report. The second aspect is the performance of an CAD/AI algorithm on the image. Tracheal pathology, if detected by an AI algorithm, would be imputed into this section of the radiology report. If the AI algorithm determines that the trachea is normal, then "normal" would be inputted into the report, which is the case in this example.

The second time interval during the image interpretation is the time period from 3.00 seconds to 9.00 seconds. The image displayed during the entirety of this period is the zoomed in image with dual windowing on the trachea. Note that the user can override this option if he/she chooses. The report item of "normal" is entered in at the report. The timer-dependent refresh rate utilized for this second time interval is comprised of two components. Both of the timer-dependent image refresh rates have to be satisfied in order to achieve wherein a new image can appear. The first component of the timer-dependent image refresh rate is a minimum delay for 3.00 seconds. The second component of the timer-dependent image refresh rate is a minimum of 10 fixation points. In this example, the user performed 5 fixation points by the time point of 3.00 seconds. It takes the user another 3.00 seconds to reach 10 fixation points. So, only at 6.00 seconds of this time period (and time mark 9.00 seconds) is the second timer-dependent image refresh rate component satisfied. The location of the fixation points during this time interval is shown. Thus, in this example, the rate limiting event is the second component. The completion of the timer-dependent refresh rate criteria acts as a triggering event for both the second image-dependent viewing parameter and the second image-dependent reporting parameter, which are therefore both implemented at 9.00 seconds. At time mark 9.00 seconds, both aspects of the image-dependent viewing parameter at this moment are implemented. Zooming setting is selected in order to maximize detection of pathology occurring within the lungs. The image-dependent viewing parameter is zooming in an dual windowing. Please see U.S. Pat. No. 10,586,400 and U.S. patent application Ser. No. 16/785,506 for details on how to perform the dual-windowing technique. The dual windowing setting shown in this example has a window level of 10,000 and a window width of 30,000 for the lungs. For all other structures in the field of view, a window level setting of 50,000 and window width setting of 120,000 is implemented. Also, please note that a halo is utilized to gradually show transition between the two different window width and window level settings. At time mark 9.00 seconds, both aspects of the image-dependent reporting parameter are implemented. The first aspect is the automatic transition into the lungs section of the radiology report. The second aspect is the performance of an CAD/AI algorithm on the image. Lung pathology, if detected by an AI algorithm, would be imputed into this section of the radiology report. If the AI algorithm determines that the trachea is normal, then "normal" would be inputted into the report. In this case, a right lung nodule is found by the AI algorithm and "right lung pulmonary nodule" is entered into the lung section of the report.

The third time interval during the image interpretation is the time period from 9.00 seconds to 20.00 seconds. The image displayed during the entirety of this period is the zoomed in image with dual windowing on the lungs. Note that the user can override this option if he/she chooses. The report item of "right lung pulmonary nodule" is entered in at the report. The timer-dependent refresh rate utilized for this third time interval is comprised of three components. All three of the timer-dependent image refresh rates have to be satisfied in order to achieve wherein a new image can appear. The first component of the timer-dependent image refresh rate is a minimum delay for 8.00 seconds. The second component of the timer-dependent image refresh rate is a minimum of 12 fixation points.

The third component of the timer-dependent image refresh rate is a minimum of 1 fixation point within 4 cm of each pixel on the screen corresponding to lung tissue. In this example, the user performed 12 fixation points by the time point of 8.00 seconds thereby satisfying the first component and second component; however, the third component of 1 fixation point within 4 cm of each pixel on the screen corresponding to lung tissue is not yet met. It takes the user another 3.00 seconds to meet the third component. By the time at which the third component is met, a total of 20 fixation points and 11.00 seconds have passed. So, only at 11.00 seconds of this time period (and time mark 20.00 seconds) is the third component of the timer-dependent image refresh rate satisfied. The location of the fixation points during this time interval is shown. Thus, in this example, the rate limiting event is the third component. Note that an annotation (e.g., red circle) could be shown over the right lung pulmonary nodule during at least some portion of this time period. Another example markup of the image would be a timer (e.g., count down of minimum time required to spend). The completion of the timer-dependent refresh rate criteria acts as a triggering event for both the third image-dependent viewing parameter and the third image-dependent reporting parameter, which are therefore both implemented at 20.00 seconds. At time mark 20.00 seconds, both aspects of the image-dependent viewing parameter at this moment are implemented. Zooming setting is selected in order to maximize detection of pathology occurring within the heart. The image-dependent viewing parameter is zooming in and dual windowing. Please see U.S. Pat. No. 10,586,400 and U.S. patent application Ser. No. 16/785,506 for details on how to perform the dual-windowing technique. The dual windowing setting shown in this example has a window level of 5,000 and a window width of 30,000 for the heart. For all other structures in the field of view, a window level setting of 50,000 and window width setting of 120,000 is implemented. Also, please note that a halo is utilized to gradually show transition between the two different window width and window level settings. At time mark 20.00 seconds, both aspects of the image-dependent reporting parameter are implemented. The first aspect is the automatic transition into the heart section of the radiology report. The second aspect is the performance of an CAD/AI algorithm on the image. Heart pathology, if detected by an AI algorithm, would be inputted into this section of the radiology report. If the AI algorithm determines that the heart is normal, then "normal" would be inputted into the report. In this case, a no pathology is found by the AI algorithm and "normal" is entered into the heart section of the report.

The fourth time interval during the image interpretation is the time period from 20.00 seconds to 25.00 seconds. The image displayed during the entirety of this period is the zoomed in image with dual windowing on the heart. Note that the user can override this option if he/she chooses. The report item of "normal" is entered in at the report. The timer-dependent refresh rate utilized for this fourth time interval is comprised of two components. Both of the timer-dependent image refresh rates have to be satisfied in order for the examination to be completed (or alternatively, additional checklist items such as the bones, upper abdomen, etc. to be performed). The first component of the timer-dependent image refresh rate is a minimum delay for 5.00 seconds. The second component of the timer-dependent image refresh rate is a minimum of 15 fixation points (as determined by an eye tracking system). In this example, the user performed exactly 15 fixation points by the time point of 5.00 seconds thereby satisfying the first component and second component simultaneously. So, at 5.00 seconds of this time period (and time mark 25.00 seconds) is the timer-dependent image refresh rate satisfied. The location of the fixation points during this time interval is shown.

The completion of the timer-dependent refresh rate criteria acts as a triggering event for the examination to be completed (or alternatively, additional checklist items such as the bones, upper abdomen, etc. to be performed).

This example therefore illustrates the interleaving of eye tracking with fixation points and multiple different types of triggering events. In this example, the user would just need to look at the screen. Over the 25 second period that follows, once the minimum time periods and fixation points occur, the image would be optimized for each anatomic structure on the checklist (e.g., zoom, window and level) and the report would automatically be filled in in steps. In this example, the user did not override (or turn off) the triggering events and the adjustment of the image parameters and report generation was automated and user eye tracking was factored in. Facial recognition could also be implemented into this overall system and used as a triggering event. It is possible that the face reacts to a dangerous finding in a predictable way, which can be factored in. Further, it is possible that inattentiveness can be picked out on facial recognition. In addition EEG analysis of the user can be performed as well and utilized as a triggering event.

Additional options include wherein the user could speed up or slow down the timer. The user could also take over manual control (e.g. alter text in report). User take over could be accomplished by keyboard input, mouse input, controller input or voice recognition input. The user can also perform zooming and panning on his own and eye tracking performed in accordance with methods disclosed in U.S. Patent Application 62/985,363. In addition, AI controlled panning and zooming integrated with eye tracking metrics can also be performed. Additionally, reporting metrics including the number of fixation points can be incorporated including the number of fixation points overall and the number of fixation points per structure.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed:

1. A method of reviewing images comprising:
    performing an analysis of an image set
        wherein said image set comprises a medical imaging examination,
        wherein said analysis of said image set comprises at least one of the group consisting of:
            a computer aided detection (CAD) algorithm; and
            an artificial intelligence (AI) algorithm,
        wherein each image from said image set is classified by said analysis to be normal or abnormal, and
        wherein said image set comprises at least one image that is classified by said analysis to be abnormal;
    assigning predetermined responses for images classified as abnormal
        wherein a predetermined response is assigned based on an abnormality classified by said analysis,
        wherein a predetermined response comprises at least a timer-dependent refresh rate, and
        wherein said timer-dependent refresh rate is associated with a length of time that an image is displayed;
    presenting images from said image set to a user on a display
        wherein when an image classified as normal is presented to said user on said display, said image classified as normal is presented to said user on said display at a user-controlled image refresh rate, and
        wherein when an image classified as abnormal is presented to said user on said display, an assigned predetermined response occurs which causes said image classified as abnormal to be presented in accordance with said assigned predetermined response which comprises at least said assigned timer-dependent refresh rate.

2. The method of claim 1 further comprising wherein the user controlled image refresh rate is performed by at least one of the group comprising: a rollerball on the mouse; a scroll wheel on a mouse; a click and drag movement on a mouse; and, keys on a keyboard.

3. The method of claim 1 further comprising wherein said at least one image that is classified by said analysis to be abnormal is classified as abnormal based on at least one of the group of: an aspect of patient metadata; user eye tracking metrics; report elements; and, user facial recognition metrics.

4. The method of claim 1 further comprising wherein the timer-dependent image refresh rate comprises at least one of the group of comprising:
    a first timer-dependent image refresh rate causes pausing at a single image for a minimum period of time wherein after the minimum period of time has passed, the refresh rate the user-controlled refresh rate resumes;
    a second timer-dependent image refresh rate utilized for at least two consecutive images wherein the second timer-dependent image refresh rate is slower than the user-controlled refresh rate;
    a third timer-dependent image refresh rate utilized for at least two consecutive images wherein the third timer-dependent image refresh rate is faster than the user-controlled refresh rate;
    a fourth timer-dependent image refresh rate utilized only a limited number of times, such that after the limited number of times is exceeded, the refresh rate is user-controlled;
    a fifth timer-dependent image refresh rate wherein the fifth timer-dependent image refresh rate is variable wherein a first image refresh rate is utilized when a first set of images are first presented and wherein a second image refresh rate is utilized when the first set of images are second presented;
    a sixth timer-dependent image refresh rate wherein the sixth timer-dependent image refresh rate is user-dependent wherein a first set of images is presented to a first user at a first timer-dependent image refresh rate and the first set of images is presented to a second user at a second timer-dependent image refresh rate; and
    a seventh timer-dependent refresh rate wherein the seventh timer-dependent image refresh rate is independent of the user-controlled image refresh rate.

5. The method of claim 1 further comprising wherein a user notification is presented when said predetermined response occurs wherein the user notification comprises at least one of the group of: visual annotation marker on the image; visual image manipulation techniques; auditory notification; and, tactile notification.

6. The method of claim 1 further comprising wherein the images comprise at least one of the group comprising: cross-sectional images; volume rendered images; and, images displayed on an extended reality headset.

7. A method comprising:
    performing an analysis of an image set
        wherein said image set comprises a medical imaging examination,
        wherein said analysis of said image set comprises at least one of the group consisting of:
            a computer aided detection (CAD) algorithm; and
            an artificial intelligence (AI) algorithm,
        wherein each image from said image set is classified by said analysis to be normal or abnormal, and
        wherein said image set comprises at least one image that is classified by said analysis to be abnormal;
    assigning predetermined responses for images classified as abnormal
        wherein a predetermined response is assigned based on an abnormality classified by said analysis,
        wherein a predetermined response comprises at least an image-dependent viewing parameter, and
        wherein said image-dependent viewing parameter introduces a visual representation of an image;
    presenting images from said image set to a user on a display
        wherein when an image classified as normal is presented to said user on said display, said image classified as normal is presented to said user on said display at a user-controlled viewing parameter, and
        wherein when an image classified as abnormal is presented to said user on said display, an assigned predetermined response occurs which causes said image classified as abnormal to be presented in accordance with said assigned predetermined response which comprises at least said assigned image-dependent viewing parameter.

8. The method of claim 7 further comprising wherein the user-controlled viewing parameter is
performed by at least one of the group comprising:
a user-performed strike of a hotkey on a keyboard;
a user-performed click and drag movement on a mouse;
a user-performed movement of a scroll wheel on a mouse; and
a user-performed point and click on a drop down menu;
to achieve at least one of the group comprising:
a user-desired window and level setting;
a user-desired false color setting;
a user-desired zoom setting;
a user-desired image rotation position;
a user-desired convergence point;
a user-desired viewing angle setting; and
a user-desired manipulation of voxels.

9. The method of claim 7 further comprising wherein said at least one image that is classified by said analysis to be abnormal is classified as abnormal based on at least one of the group of: an aspect of patient metadata; user eye tracking metrics; report elements; and, user facial recognition metrics.

10. The method of claim 7 further comprising wherein the image-dependent viewing parameter comprises at least one of the group of comprising:
a first image-dependent viewing parameter wherein the first image-dependent viewing parameter is a window width and window level setting for the entire dataset;
a second image-dependent viewing parameter wherein the second image-dependent viewing parameter includes setting a window and level parameter for a first image slice independently from a window and level parameter for a second image slice;
a third image-dependent viewing parameter wherein the third image-dependent viewing parameter includes displaying simultaneously a first visual representation adjustment logic for a first segmented structure and a second visual representation adjustment logic for a second segmented structure wherein the first visual representation adjustment logic is different from the second visual representation adjustment logic;
a fourth image-dependent viewing parameter wherein the fourth image-dependent viewing parameter is a false color setting;
a fifth image-dependent viewing parameter wherein the fifth image-dependent viewing parameter is a zoom setting;
a sixth image-dependent viewing parameter wherein the sixth image-dependent viewing parameter is an image rotation setting;
a seventh image-dependent viewing parameter wherein the seventh image-dependent viewing parameter is a viewing angle setting; and
an eighth image-dependent viewing parameter wherein the eight image-dependent viewing parameter includes advanced image processing techniques.

11. The method of claim 7 further comprising wherein a user notification is presented when said predetermined response occurs wherein the user notification comprises at least one of the group of: visual annotation marker on the image; visual image manipulation techniques; auditory notification; and, tactile notification.

12. The method of claim 7 further comprising wherein the images comprise at least one of the group comprising: cross-sectional images; volume rendered images; and, images displayed on an extended reality headset.

13. A method comprising:
performing an analysis of an image set
wherein said image set comprises a medical imaging examination,
wherein said analysis of said image set comprises at least one of the group consisting of:
a computer aided detection (CAD) algorithm; and
an artificial intelligence (AI) algorithm,
wherein each image from said image set is classified by said analysis to be normal or abnormal, and
wherein said image set comprises at least one image that is classified by said analysis to be abnormal;
assigning predetermined responses for images classified as abnormal
wherein a predetermined response is assigned based on an abnormality classified by said analysis,
wherein a predetermined response comprises at least an image-dependent reporting parameter, and
wherein said image-dependent reporting parameter introduces an alteration of text within a report in an image reporting system;
presenting an image reporting system to a user
wherein when an image classified as normal is presented to said user on said display, text within said image reporting system is altered with user-controlled reporting parameters, and
wherein when an image classified as abnormal is presented to said user on said display, an assigned predetermined response occurs which causes said image reporting system to execute said assigned predetermined response which comprises at least said assigned image-dependent reporting parameter.

14. The method of claim 13 further comprising wherein the user-controlled reporting parameter is
performed by at least one of the group comprising:
a user-performed strike of a button on a microphone;
a user-performed strike of a hotkey on a keyboard;
a user-performed click and drag movement on a mouse;
a user-performed movement of a scroll wheel on a mouse; and
a user-performed point and click on a drop down menu;
to achieve at least one of the group comprising:
a user-desired input of text;
a user-desired alteration of text;
a user-desired deletion of text; and
a user-desired navigation from a first section of a report to a second section of a report.

15. The method of claim 13 further comprising wherein said at least one image that is classified by said analysis to be abnormal is classified as abnormal based on at least one of the group of: an aspect of patient metadata; user eye tracking metrics; and, user facial recognition metrics.

16. The method of claim 13 further comprising wherein the image-dependent reporting parameter comprises at least one of the group of comprising:
a first image-dependent reporting parameter wherein text is automatically inputted into a section of a report;
a second image-dependent reporting parameter wherein text in a section of a report is automatically altered;
a third image-dependent reporting parameter wherein text in a section of a report is automatically deleted; and a fourth image-dependent reporting parameter wherein a cursor is automatically moved from a first section of a report to a second section of a report.

17. The method of claim 13 further comprising wherein a user notification is presented when said predetermined response occurs wherein the user notification comprises at least one of the group of: visual annotation marker on the image; visual image manipulation techniques; auditory notification; and, tactile notification.

18. The method of claim 13 further comprising wherein the images comprise at least one of the group comprising: cross-sectional images; volume rendered images; and, images displayed on an extended reality headset.

19. The method of claim 13 further comprising wherein said predetermined response further comprises at least one of the group consisting of:
   a timer-dependent refresh rate; and
   an image-dependent viewing parameter.

20. A method of reviewing images comprising:
   performing an analysis of an image set
      wherein said image set comprises a medical imaging examination,
      wherein said analysis of said image set comprises at least one of the group consisting of:
         a computer aided detection (CAD) algorithm; and
         an artificial intelligence (AI) algorithm,
      wherein each image from said image set is classified by said analysis to be normal or abnormal, and
      wherein said image set comprises at least one image that is classified by said analysis to be abnormal;
   assigning predetermined responses for images classified as abnormal wherein based on an abnormality classified by said analysis,
      a first predetermined response is assigned wherein said first predetermined response comprises at least a timer-dependent refresh rate, and wherein said timer-dependent refresh rate is associated with a length of time that an image is displayed, and
      a second predetermined response is assigned wherein said second predetermined response comprises at least an image-dependent viewing parameter, and wherein said image-dependent viewing parameter introduces a visual representation of an image,
   presenting images from said image set to a user on a display
      wherein when an image classified as normal is presented to said user on said display, said image classified as normal is presented to said user on said display at a user-controlled image refresh rate and user-controlled viewing parameter,
      wherein when an image classified as abnormal is presented to said user on said display, an assigned predetermined response occurs which causes said image classified as abnormal to be presented in accordance with said assigned predetermined response which comprises at least said timer-dependent refresh rate and said assigned image-dependent viewing parameter.

* * * * *